(12) United States Patent
Martin et al.

(10) Patent No.: US 7,935,065 B2
(45) Date of Patent: May 3, 2011

(54) ORAL DEVICE

(75) Inventors: Ruth E. Martin, London (CA); Frank Bihari, London (CA); Julie A. Theurer, London (CA); Rebecca C. Smith, London (CA)

(73) Assignee: The University of Western Ontario, London (CA)

( * ) Notice: Subject to any disclaimer, the term of this patent is extended or adjusted under 35 U.S.C. 154(b) by 852 days.

(21) Appl. No.: 11/411,241

(22) Filed: Apr. 26, 2006

(65) Prior Publication Data

US 2006/0282010 A1 Dec. 14, 2006

Related U.S. Application Data

(60) Provisional application No. 60/676,942, filed on May 3, 2005.

(51) Int. Cl.
*A61B 5/103* (2006.01)
*A61B 5/117* (2006.01)
(52) U.S. Cl. ......... 600/590; 600/587; 600/589; 600/593
(58) Field of Classification Search .................. 600/237, 600/560, 587, 589, 590, 553, 593, 595
See application file for complete search history.

(56) References Cited

U.S. PATENT DOCUMENTS

| | | | |
|---|---|---|---|
| 3,853,105 A | 12/1974 | Kenagy | |
| 4,071,026 A * | 1/1978 | Bevins | 128/205.29 |
| 4,170,230 A * | 10/1979 | Nelson | 128/859 |
| 4,572,177 A | 2/1986 | Tiep et al. | |
| 4,576,190 A | 3/1986 | Youssef | |
| 4,676,774 A | 6/1987 | Semm et al. | |
| 4,679,551 A | 7/1987 | Anthony | |
| 4,773,898 A | 9/1988 | Begouen | |
| 4,790,305 A | 12/1988 | Zoltan et al. | |
| 4,996,990 A | 3/1991 | Hideshima | |
| 5,066,502 A | 11/1991 | Eales | |
| 5,085,634 A | 2/1992 | Lackney | |
| 5,143,087 A | 9/1992 | Yarkony | |
| 5,147,298 A | 9/1992 | Turner et al. | |
| 5,176,151 A | 1/1993 | Harding | |

(Continued)

FOREIGN PATENT DOCUMENTS

CA 2064882 2/1991

(Continued)

OTHER PUBLICATIONS

Office Action from Chinese Application No. 200680014928.9, dated Mar. 6, 2009, 5 pgs.

(Continued)

*Primary Examiner* — Max Hindenburg
*Assistant Examiner* — Adam J Eiseman
(74) *Attorney, Agent, or Firm* — Brinks Hofer Gilson & Lione

(57) ABSTRACT

An oral device for use with a person in which at least one non-toxic gas pulse is delivered to a predetermined location in the mouth via a device conduit. The oral device may be provided as a kit with at least one device for measuring the subject's responses and representing them as feedback to the subject/clinician. A method of creating a gas bolus pulse train, delivering it to a predetermined mouth area, and monitoring the subject's responses to it, is also shown. The oral device and method may be used as a diagnostic tool, or a therapeutic tool, in swallowing or speech rehabilitation of children and adults who have swallowing, speech, salivary, and/or oral sensorimotor impairments.

31 Claims, 11 Drawing Sheets

U.S. PATENT DOCUMENTS

| | | | |
|---|---|---|---|
| 5,213,553 | A | 5/1993 | Light |
| 5,377,688 | A | 1/1995 | Aviv et al. |
| 5,515,860 | A | 5/1996 | Aviv et al. |
| H1557 | H | 7/1996 | Joubert et al. |
| 5,566,645 | A | 10/1996 | Cole |
| 5,649,540 | A | 7/1997 | Alvarez et al. |
| 5,725,564 | A | 3/1998 | Freed et al. |
| 5,735,772 | A | 4/1998 | Schiavoni |
| 5,826,570 | A | 10/1998 | Goodman et al. |
| 5,855,908 | A | 1/1999 | Stanley et al. |
| 5,884,625 | A | 3/1999 | Hart .................. 128/207.14 |
| 5,891,185 | A | 4/1999 | Freed et al. |
| 5,897,492 | A | 4/1999 | Feller et al. |
| 5,950,624 | A | 9/1999 | Hart .................. 128/207.15 |
| 5,954,673 | A | 9/1999 | Staehlin et al. |
| 5,970,978 | A | 10/1999 | Aviv et al. |
| 5,987,359 | A | 11/1999 | Freed et al. |
| 5,993,413 | A | 11/1999 | Aaltonen et al. |
| 6,036,655 | A | 3/2000 | Aviv et al. |
| D422,694 | S | 4/2000 | Hill |
| 6,104,958 | A | 8/2000 | Freed et al. |
| 6,264,058 | B1 | 7/2001 | Porter et al. |
| 6,295,988 | B1 | 10/2001 | Sue .................. 128/859 |
| 6,299,592 | B1 | 10/2001 | Zander |
| 6,355,003 | B1 | 3/2002 | Aviv et al. |
| 6,371,758 | B1 | 4/2002 | Kittelsen |
| 6,454,788 | B1 | 9/2002 | Ashton |
| 6,484,053 | B2 | 11/2002 | Leelamanit |
| 6,591,140 | B2 * | 7/2003 | Strome et al. .................. 607/61 |
| 6,607,549 | B2 | 8/2003 | Huang |
| 6,805,127 | B1 | 10/2004 | Karasic .................. 128/861 |
| 6,916,287 | B2 | 7/2005 | Dematteis et al. |
| 6,935,857 | B1 | 8/2005 | Farrell |
| 6,960,183 | B2 * | 11/2005 | Nicolette .................. 604/57 |
| 7,021,930 | B2 | 4/2006 | Schemmer et al. |
| 7,039,468 | B2 | 5/2006 | Freed et al. |
| 7,083,548 | B1 | 8/2006 | Moore et al. |
| 7,118,377 | B2 | 10/2006 | Inoue et al. |
| 7,147,468 | B2 | 12/2006 | Snyder et al. |
| 7,238,145 | B2 | 7/2007 | Robbins et al. |
| 7,239,918 | B2 | 7/2007 | Strother et al. |
| 7,273,327 | B2 | 9/2007 | Hohlbein et al. |
| 7,357,633 | B2 | 4/2008 | Mailyan |
| 7,477,947 | B2 | 1/2009 | Pines et al. |
| 7,660,636 | B2 | 2/2010 | Castel et al. |
| 2002/0082544 | A1 | 6/2002 | Thrash |
| 2003/0015198 | A1 | 1/2003 | Hecke et al. .................. 128/204.18 |
| 2003/0104342 | A1 | 6/2003 | Lynch et al. |
| 2004/0000054 | A1 | 1/2004 | Sommer |
| 2004/0028676 | A1 | 2/2004 | Klein et al. |
| 2004/0138585 | A1 | 7/2004 | Dematteis et al. |
| 2005/0222535 | A1 | 10/2005 | Uesugi et al. |
| 2006/0110710 | A1 | 5/2006 | Schemmer et al. .................. 433/224 |
| 2006/0210480 | A1 | 9/2006 | Hamdy |
| 2006/0235352 | A1 | 10/2006 | Dziewas |
| 2006/0282010 | A1 | 12/2006 | Martin et al. |
| 2007/0156182 | A1 | 7/2007 | Castel et al. |
| 2008/0009810 | A1 | 1/2008 | Hamdy |
| 2008/0077192 | A1 | 3/2008 | Harry et al. |
| 2008/0147141 | A1 | 6/2008 | Testerman et al. |
| 2008/0147142 | A1 | 6/2008 | Testerman et al. |
| 2008/0251597 | A1 | 10/2008 | Pearson |
| 2008/0269837 | A1 | 10/2008 | Ludlow et al. |
| 2008/0269856 | A1 | 10/2008 | Cross et al. |
| 2008/0269857 | A1 | 10/2008 | Cross et al. |
| 2008/0269858 | A1 | 10/2008 | Cross et al. |
| 2008/0269859 | A1 | 10/2008 | Cross et al. |
| 2008/0269860 | A1 | 10/2008 | Cross et al. |
| 2008/0269861 | A1 | 10/2008 | Cross et al. |
| 2009/0018611 | A1 | 1/2009 | Campbell et al. |
| 2009/0048645 | A1 | 2/2009 | Philipp et al. |
| 2009/0048647 | A1 | 2/2009 | Tingey |
| 2009/0054980 | A1 | 2/2009 | Ludlow et al. |
| 2009/0120446 | A1 | 5/2009 | Vaska et al. |
| 2009/0120447 | A1 | 5/2009 | Vaska et al. |
| 2009/0123886 | A1 | 5/2009 | Vaska |
| 2009/0137859 | A1 | 5/2009 | Belafsky et al. |
| 2009/0249571 | A1 | 10/2009 | Rohrig |
| 2009/0259310 | A1 | 10/2009 | Blom |
| 2009/0286237 | A1 | 11/2009 | Fitzgerald et al. |
| 2009/0306626 | A1 | 12/2009 | Sinha et al. |
| 2009/0306741 | A1 | 12/2009 | Hogle et al. |
| 2010/0010400 | A1 | 1/2010 | Martin et al. |
| 2010/0016908 | A1 | 1/2010 | Martin et al. |
| 2010/0055233 | A1 | 3/2010 | Macinnis et al. |
| 2010/0121224 | A1 | 5/2010 | Toyota et al. |

FOREIGN PATENT DOCUMENTS

| | | |
|---|---|---|
| CA | 2203257 | 5/1996 |
| EP | 1 314 430 B1 | 9/2007 |
| JP | 11309186 A * | 11/1999 |
| WO | WO 90/10470 A1 | 9/1990 |
| WO | WO 02/38012 A2 | 5/2002 |
| WO | WO 03/061453 A2 | 7/2003 |
| WO | WO 03614539 A2 | 7/2003 |
| WO | WO 2004/028433 A2 | 4/2004 |
| WO | WO 2004/028433 A3 | 4/2004 |
| WO | WO 2004/069076 A2 | 8/2004 |
| WO | WO 2004/075743 A1 | 9/2004 |
| WO | WO 2005/070316 A1 | 8/2005 |
| WO | WO 2005/102458 A2 | 11/2005 |
| WO | WO 2005/122877 A1 | 12/2005 |
| WO | WO 2006/024825 A1 | 3/2006 |
| WO | WO 2006/083217 A1 | 8/2006 |
| WO | WO 2006/106327 A1 | 10/2006 |
| WO | WO 2006/108066 A2 | 10/2006 |
| WO | WO 2006/116843 A1 | 11/2006 |
| WO | WO 2006/108066 A3 | 12/2006 |
| WO | WO 2007/005582 A1 | 1/2007 |
| WO | WO 2007/021468 A2 | 2/2007 |
| WO | WO 2007/021468 A3 | 2/2007 |
| WO | WO 2007/022034 A2 | 2/2007 |
| WO | WO 2007/081764 A2 | 7/2007 |
| WO | WO 2007/081764 A3 | 7/2007 |
| WO | WO 2007/123746 A2 | 11/2007 |
| WO | WO 2007/123746 A3 | 11/2007 |
| WO | WO 2008/076646 A1 | 6/2008 |
| WO | WO 2009/127947 A2 | 10/2009 |

OTHER PUBLICATIONS

European Search Report for EP Application No. 06721849.5-2319, dated Feb. 18, 2010, 5 pgs.

International Search Report for PCT Application No. PCT/CA2006/000650, dated Sep. 6, 2006, 2 pgs.

International Search Report for PCT Application No. PCT/IB 2009/005252, dated Oct. 7, 2006, 5 pgs.

Gross, Roxann D. et al., "Lung Volume Effects On Pharyngeal Swallowing Physiology", *J. Appl. Physiol*, vol. 95, 2003, pp. 2211-2217.

Hiraba, Hisao et al. "Increased Secretion of Salivary Glands Produced by Facial Vibrotactile", *Somatosensory and Motor Research*, vol. 25, 2008, pp. 222-229.

Jafari, Samah et al. "Sensory Regulation of Swallowing and Airway Protection: A Role For The Internal Superior Layngeal Nerve in Humans", *J. Physiol*, vol. 550, No. 1, 2003. pp. 287-304.

Logemann, Jeri A., "The Effects of VitalStim on Clinical Research Thinking in Dysphagia", *Dysphagia*, No. 22, 2007 pp. 11-12.

Lowell, Soren et al., "Sensory Stimulation Activates Both Motor and Sensory Components of the Swallow System", *NeuroImage*, vol. 42, 2008, pp. 295-295.

Lowell, Soren et al., "The Effects of Sensory Stimulation on Urge and Frequency of Swallowing", *PPT Presentation made at the 2008 meeting of the Dysphagia Research Society*, National Institutes of Heath, 2008, 14 pgs.

Pamphlet by PENTAX, ENT Scopes, 2005, 2 pgs.

Sörös, P. et al., "Functional MRI of Oropharyngeal Air-Pulse Stimulation", *Neuroscience*, vol. 53, 2008, pp. 1300-1308.

Theurer, Julie et al. "The Effects of Oropharyngeal Air-Pulse Stimulation on Swallowing in Healthy Older Adults", *Dysphagia*, 2009, 12 pgs.

Program of the 103$^{rd}$ Meeting of the Acoustical Society of America, *J. Acoust. Am.*, 1982, Suppl. 1, vol. 71 pp. S1-S113.

Ali, Galib N. et al., "Influence of Cold Stimulation on the Normal Pharyngeal Swallow Response", *Dysphagia*, 1996, vol. 11, pp. 2-8.

Aviv, Jonathan E. et al., "Air Pulse Quantification of Supraglottic and Pharyngeal Sensation: A New Technique", *Ann Otol Rhinol Laryngol*, 1993, vol. 102, pp. 777-780.

Aviv, Jonathan E. et al., "Clinical assessment of Pharyngolaryngeal Sensitivity", *The American Journal of Medicine*, 2000, vol. 108 (4A), pp. 68S-72S.

Aviv, Jonathan E. et al., "Effects of Aging on Sensitivity of the Pharyngeal and Supraglottic Areas", *The American Journal of Medicine*, 1997, vol. 103 (5A), pp. 74S-76S.

Aviv, Jonathan E. et al., "Laryngopharyngeal Sensory Deficts in Patients with Laryngopharyngeal Reflux and Dysohagia", *Ann Otol Rhinol Laryngol*, 2000, vol. 109, pp. 1000-1006.

Aviv, Jonathan E. et al., "Laryngopharyngeal Sensory Discrimination Testing and the Laryngeal Adductor Reflex", *Ann Otol Rhinol Laryngol*, 1999, vol. 108, pp. 725-730.

Aviv, Jonathan E. et al., "Silent Laryngopharyngeal Sensory Deficits After Stroke", *Ann Otol Rhinol Laryngol*, 1997, vol. 106, pp. 87-93.

Aviv, Jonathan E. et al., "Supraglottic and Pharyngeal sensory Abnormalities in Stroke patients with Dysphagia", *Ann Otol Rhinol Laryngol*, 1996, vol. 105, pp. 92-97.

Balzamo, E. et al., "Short-latency components of evokes potentials to median nerve stimulation recorded by intracerebral electrodes in the human pre- and postcentral areas", *Clinical Neurophysiology*, 2004, vol. 115, pp. 1616-1623.

Barberi, Enzo A. et al., "A Transmit-Only/Receive-Only (TORO) RF System for High-Field MRI/MRS Applications", *Magnetic Resonance in Medicine*, 2000, Vil. 43, pp. 284-289.

Beckmann, Christian F. et al., "Probabilistic Independent Component Analysis for Functional Magnetic Resonance Imaging", *IEEE Transactions on medical Imaging*, 2004, vol. 23, No. 2. pp. 137-152.

Bessho, H. et al., "Localization of Palatal Area in Human Somatosensory Cortex", *J Dent Res*, 2007, vol. 86, No. 3, pp. 265-270.

Boliek, C. E. et al., "Establishing a reliable protocol to measure tongue sensation", *Journal of Oral Rehabilitation*, 2007, vol. 34, pp. 433-441.

Bourdiol, P. et al., "Effect of age on salivary flow obtained under feeding and non-feeding conditions", *Journal of Oral Rehabilitation*, 2004, vol. 31, pp. 445-452.

Bove, Mogens et al., "Thermal Oral-Pharyngeal Stimulation and Elicitation of Swallowing", *Acta Otolaryngol (Stochk)*, 1998, vol. 118. pp. 728-731.

Broekhuusen M. L. et al., "Factors Influencing jaw Position Sense in Man", *Archs oral Biol.*, 1983, vol. 28, No. 5, pp. 387-391.

Calhoun, Karen K. et al., "Age-Related Changes in Oral Sensation", *Laryngoscope*, 1992, vol. 102, pp. 109-116.

Capra, Norman F., "Mechanism of Oral Sensation", *Dysphagia*, 1995, vol. 10, pp. 235-247.

Cook, I. J. et al., "Influence of aging on oral-pharyngeal bolus transit and clearance during swallowing: scintigraphic study", *The American Physiological Society*, 1994, pp. G972-G977.

Craig, A. D. et al., "Thermosensory activation of insular cortex", 2000, *Nature Neuroscience*, vol. 3, No. 2, pp. 184-190.

Dale et al. "Cortical Surface-Based Analysis", *NeuroImage*, 1999, vol. 9, pp. 179-194.

Darian-Smith, I. et al., "Somatic Sensory Cortical Projection Areas Excited by Tactile Stimulation of the Cat: A Triple Representation", *J. Physiol.*, 1966, vol. 182. pp. 671-689.

Dawes, C., "Circadian Rhythms in Human Salivary Flo Rate and Composition", *J. Physiol.*, 1972, vol. 220. pp. 529-545.

Dawes, C. et al., "Circadian Rhythms in the Flow Rate and Proportional Contribution of Parotid to Whole Saliva Volume in Man", *Arch oral Biol.*, 1973, vol. 18. pp. 1145-1153.

Ding, Ruiying et al., "The Effects of taste and Consistency on Swallow Physiology in Younger and Older Healthy Individuals: A Surface Electromyographic Study", *Journal of Speech, Language, and Hearing Research*, 2003, vol. 46, pp. 977-989.

Disbrow, Elizabeth A. et al., "Ipsilateral Representation of Oral Structures in Human Anterior Parietal Somatosensory Cortex and Integration of Inputs Across the Midline", *The Journal of Comparative Neurology*, 2003, vol. 467, pp. 487-495.

Do, David H. et al., "Resolving Subjects and Measuring Observer/Subject Distances with a Thermal Tactile Imager", *IEEE*, 30th Annual International IEEE EMBS Conference, Vancouver, Canada, 2008, pp. 4302-4305.

Doty, Robert W., "Influence of Stimulus pattern on Reflex Deglutition", *Dept. Of Physiology, The University of Chicago*, 1951, vol. 166, pp. 142-158.

Dum, Richard R. et al., "Motor areas in the frontal lobe of the primate", *Physiology and Behavior*, 2002, vol. 77, pp. 677-682.

Fabri, Mara et al., "Bulateral Cortical Representation of the Trunk Midline in Human First Somatic Sensory Area", *Human Brain Mapping*, 2005, vol. 25, pp. 287-296.

Ferguson D. B. et al., "Circadian Rhythms in Human Partotid Saliva Flow Rate and Composition", *Archs oral Biol.*, 1973, vol. 18. pp. 1155-1173.

Flynn, Frederick et al., "Anatomy of the insula-functional clinical correlates", *Aphasiology*, 1999, vol. 13, No. 1, pp. 55-78.

Fraser, Chris et al., "Driving Plasticity in Human Adult Motor Cortex is Associated with Improved Motor Function after Brain Injury", *Neuron*, 2002, vol. 34, pp. 831-840.

Fukunaga, Akiko et al., "Influences of Aging on Taste Perception and Oral Somatic Sensation", *Journal of Gerontology: Medical Sciences*, 2005, vol. 60A, No. 1, pp. 109-113.

Gemba, Hisae et al., "Influences of emotion upon parotid secretion in human", *Neuroscience Letters*, 1996, vol. 211, pp. 159-162.

Hamdy, Shaheen et al., "Cranial nerve modulation of human cortical swallowing motor pathways", *American Physiological Society*, 1997, pp. G802-G808.

Hamdy, Shaheen et al., "Explaining oropharyngeal dysphagia after unilateral hemispheric stroke", *The Lancet*, 1997, vol. 350, pp. 686-692.

Hamdy, Shaheen et al., "Long-term reorganization of human motor cortex driven by short-term sensory stimulation", *Nature America Inc.*, 1998, vol. 1, No. 1, pp. 64-68.

Hamdy, S. et al., "Modulation of human swallowing behavior by thermal and chemical stimulation in health and after brain injury", *Neurogastroenterology and Motility*, 2003, vol. 15, pp. 69-77.

Hamdy, Shaheen et al., "Recovery of Swallowing After Dysphagic Stroke Relates to Functional Reorganization in the Intact Motor Cortex", *Gastroenterology*, 1998; vol. 115, No. 5, pp. 1104-1112.

Hamdy, Shaheen et al., "The cortical topography of human swallowing musculature in health and disease", *Nature Medicine*, 1996, vol. 2, No. 11, pp. 1217-1224.

Hayashi, H. et al., "Functional Organization of Trigeminal Subnucleus Interpolaris: Nociceptive and Innocuous Afferent Inputs, Projections to Thalamus, Cerebellum, and Spinal Cord, and Descending Modulation From Periaqueductal Gray", *The American Physiological Society, Journal of Neurophysiology*, 1984, vol. 51, No. 5, pp. 890-905.

Huang, C.-S. et al., "Input-Output Relationships of the Primary Face Motor Cortex in the Monkey (*Macaca fascicularis*)", *The American Physiological Society, Journal of Neurophysiology*, 1989, vol. 61, No. 2, pp. 350-362.

Iwamura, Yoshiaki et al., "Bilateral Activity and Callosal Connections in the Somatosensory Cortex", *The Neuroscientist*, 2001, vol. 7, No. 5, pp. 419-429.

Jacobs, Reinhilde et al., "Oral stereognosis: a review of the literature", *Clin Oral Invest*, 1998, vol. 2, pp. 3-10.

Jafari, Samah et al., "Sensory regulation of swallowing and airway protection: a role for the internal superior laryngeal nerve in humans", *The physiological Society, J Physiol*, 2003, vol. 30, No. 10, pp. 1-18.

Jaradeh, Safwan, MD, "Neurophysiology of Swallowing in the Aged", *Dysphagia*, 1994, vol. 9, pp. 218-220.

Jean, Andre, "Brain Stem Control of Swallowing: Neuronal Network and Cellular Mechanisms", *The American Physiological Society*, 2001, vol. 81, No. 2, pp. 929-969.

Kaatzke-McDonald, Monika N., M App Sc et al., "The Effects of Cold, Touch, and Chemical Stimulation of the Anterior Faucial Pillar on Human Swallowing", *Dysphagia*, 1996, vol. 11, pp. 198-206.

Kapila, Yagya V., MD et al., "Relationship Between Swallow Rate and Salivary Flow", *Digestive Diseases and Sciences*, 1984, vol. 29, No. 6, pp. 528-533.

Kern, Mark K. et al., "Cerebral cortical representation of reflexive and volitional swallowing in humans", *American Physiological Society, Am J Physiol Gastrointest Liver Physiol*, 2001, vol. 280, pp. G354-G360.

Kitagawa, Jun-Ichi et al., "Pharyngeal branch of the glossopharyngeal nerve plays a major role in reflex swallowing from the pharynx", *American Physiological Society, Am J Physiol Regulatory Integrative Comp Physiol*, 2002, vol. 282, pp. R1342-R1347.

Kleim, Jeffrey A. et al., "Principles of Experience-Dependent Neural Plasticity: Implications for Rehabilitation After Brain Damage", *Journal of Speech, Language, and Hearing Research*, 2008, vol. 51, pp. S225-S239.

Lagerlöf, F. et al., "The Volume of Saliva in the Mouth Before and After Swallowing", *Univ of Western Ontario*, 2009, vol. 63, No. 5, pp. 618-621.

Lazzara, Gisela de Lama, M.A. et al., "Impact of Thermal Stimulation on the Triggering of the Swallowing Reflex", *Dysphagia*, 1986, vol. 1, pp. 73-77.

Lear, C. S. C. et al., "The Frequency of Deglutition in Man", *Arch. oral Biol.*, 1965, vol. 10, pp. 83-99.

Lim, Kil-Byung, MD, PhD et al., "Neuromuscular Electrical and Thermal-Tactile Stimulation for Dysphagia Caused by Stroke: A Randomized Controlled Trial", *J Rehabil Med*, 2009, vol. 41, pp. 174-178.

Lin, L.-D. et al., "Functional Properties of Single Neurons in the Primate Face Primary Somatosensory Cortex. II. Relations With Different Directions of Trained Tongue Protrusion", *The American Physiological Society, Journal of Neurosphysiology*, 1994, vol. 71, No. 6, pp. 2391-2400.

Linden, Patricia, M.A. et al. "Bolus Position at Swallow Onset in Normal Adults: Preliminary Observations", *Dysphagia*, 1989, vol. 4, pp. 146-150.

Logemann, Jeri A. et al., "Closure mechanisms of laryngeal vestibule during swallow", *The American Physiological Society, Am. J. Physiol.*, 1992, vol. 262, pp. G338-G344.

Logemann, Jeri A., Ph.D., "Preswallow Sensory Input: Its Potential Importance to Dysphagic Patients and Normal Individuals", *Dysphagia*, 1996, vol. 11, pp. 9-10.

Logemann, Jeri A. et al., "Temporal and Biomechanical Characteristics of Oropharyngeal Swallow in Younger and Older Men", *American Speech Language-Hearing Association, Journal of Speech, Language, and Hearing Research*, 2000, vol. 43, pp. 1264-1274.

Lowell, Soren Y. et al., "Sensory stimulation activates both motor and sensory components of the swallowing system", *NeuroImage*, 2008, vol. 42, pp. 285-295.

Malenfant, Annie et al., "Tactile, thermal and pain sensibility in burned patients with and without chronic pain and paresthesia problems", *International Association for the Study of Pain*, 1998, vol. 77, pp. 241-251.

Manger, Paul R. et al., "Representation of Face and Intra-Oral Structures in Area 3b of Macaque Monkey Somatosensory Cortex", *The Journal of Comparative Nurology*, 1996, vol. 371, pp. 513-521.

Månsson, Ingemar, M.D. et al., "Effects of Surface Anesthesia on Deglutition in Man", *Department of Otorhinolaryngology, University of Gothenburg*, Sweden, 1973-1974, pp. 427-437.

Marik, Paul E., MD, FCCP et al., "Aspiration Pneumonia and Dysphagia in the Elderly", *American College of Chest Physicians, Chest*, 2003, vol. 124, pp. 328-336.

Martin, Ruth E. et al., "Cerebral Areas Processing Swallowing and Tongue Movement Are Overlapping but Distinct: A Functional Magnetic Resonance Imaging Study", *The American Physiological Society, J Neurophysiol*, 2004, vol. 92, pp. 2428-2443.

Martin, Ruth et al., "Cerebral cortical processing of swallowing in older adults", *Exp Brain Res*, 2007, vol. 176, pp. 12-22.

Martin, Ruth E. et al., "Cerebral Cortical Representation of Automatic and Volitional Swallowing in Humans", *The American Physiological Society, J Neurophysiol*, 2001, vol. 85, pp. 938-950, www.jn.physiology.org.

Martin, Ruth E. et al., "Features of Cortically Evoked Swallowing in the Awake Primate (*Macaca fascicularis*)", *The American Physiological Society, J. Neurophysiol.*, 1999, vol. 82, pp. 1529-1541.

Martin, Ruth E., "Neuroplasticity and Swallowing", *Dysphagia*, 2008.

Martin, Ruth E. et al., "The Role of the Cerebral Cortex in Swallowing", *Dysphagia*, 1993, vol. 8, pp. 195-202.

McKee, G. J. et al., "Does age or sex affect pharyngeal swallowing?", *Clinical Otolaryngology*, 1998, vol. 23, pp. 100-106.

Menon, Ravi S., "Postacquisition Suppression of Large-Vessel BOLD Signals in High-Resolution fMRI", *Magnetic Resonance in Medicine*, 2002, vol. 47, pp. 1-9.

Mese, H. et al., "Invited Review—Salivary secretion, taste and hyposalivation", *Journal of Oral Rehabilitation*, 2007, vol. 34, pp. 711-723.

Miller, Arthur J., "Deslution", *Physiological Reviews*, 1982. vol. 62, No. 1, pp. 129-184.

Miyamoto, Jun J. et al., "The Representation of the Human Oral Area in the Somatosensory Cortex: a Functional MRI Study", *Cerebral Cortex*, 2006, vol. 16, No. 5, pp. 669-675.

Mizobuchi, Keiko et al., "Single unit responses of human cutaneous mechanoreceptors to air-puff stimulation", *Clinical Neurophysiology*, 2000, vol. 111, pp. 1577-1581.

Mosier, Kristine, DMD, PhD et al., "Cortical Representation of Swallowing in Normal Adults: Functional Implications", *The American Laryngological, Rhinological and Otological Society, Inc., The Laryngoscope*, 1999, vol. 109, pp. 1417-1423.

Mu, Liancai et al., "Sensory Nerve Supply of the Human Oro- and Laryngopharynx: A Preliminary Study", *The Anatomical Record*, 2000, vol. 258, pp. 406-420.

Nakamura, Akinori et al., "Somatosensory Homunculus as Drawn by MEG", *NeuroImage*, 1998, vol. 7, pp. 377-386, Article No. NI980332.

Navazesh, M. et al., "A Comparison of Whole Mouth Resting and Stimulated Salivary Measurement Procedures", *J Dent Res*, 1982, vol. 61, No. 10, pp. 1158-1162.

Ootani, Shinji et al., "Convergence of Afferents from the SLN and GPN in Cat Medullary Swallowing Neurons", *Brain Research Bulletin*, 1995, vol. 37, No. 4, pp. 397-404.

Palmer, Jeffrey B., M.D. et al., "Coordination of Mastication and Swallowing", *Dysphagia*, 1992, vol. 7, pp. 187-200.

Pommerenke, W. T., "A Study of the Sensory Areas Eliciting the Swallowing Reflex", *The American Journal of Physiology*, 1927, vol. 81, No. 1, pp. 36-41.

Power, Macine L., PhD et al., "Evaluating Oral Stimulation as a Treatment for Dysphagia after Stroke", *Dysphagia*, 2006, pp. 49-55.

Robbins, JoAnne et al., "Swallowing and Dysphagia Rehabilitation: Translating Principles of Neural Plasticity Into Clinically Oriented Evidence", *American Speech-Language-Hearing Association, Journal of Speech, Language, and Hearing Research*, 2008, vol. 51, pp. S276-S300.

Rosenbek, John C., PhD et al., "Comparing Treatment Intensities of Tactile-Thermal Application", *Dysphagia*, 1998, vol. 13, pp. 1-9.

Rosenbek, John C., PhD et al., "Thermal Application Reduces the Duration of Stage Transition in Dysphagia after Stroke", *Dysphagia*, 1996, vol. 11, pp. 225-233.

Ruben, J. et al., "Somatotopic Organization of Human Secondary Somatosensory Cortex", *Cerebral Cortex*, 2001, vol. 11, No. 5, pp. 463-473.

Rudney, J. D. et al., "The Prediction of Saliva Swallowing Frequency in Humans From Estimates of Salivary Flow Rate and the Volume of Saliva Swallowed", *Archs oral Biol.*, 1995, vol. 40, No. 6, pp. 507-512.

Schneyer, Leon H. et al., "Rate of Flow of Human Parotid, Sublingual, and Submaxillary Secretions During Sleep", *J. D. Res.*, 1956, vol. 35, No. 1, pp. 109-114.

Sciortino, Kellie Filter, PhD, CCC-SLP et al., "Effects of Mechanical, Cold, Gustatory, and Combined Stimulation to the Human Anterior Faucial Pillars", *Dysphagia*, 2003, vol. 18, pp. 16-26.

Servos, Philip et al., "fMRI evidence for an inverted face representation in human somatosensory cortex", *NeuroReport*, 1999, vol. 10, No. 7, pp. 1393-1395.

Sessle, B. J., "Review Article, Mechanisms of oral somatosensory and motor functions and their clinical correlates", *Journal of Oral Rehabilitation*, 2006, vol. 33, pp. 243-261.

Shaffer, Scott W. et al., "Aging of the Somatosensory System: A translational Perspective", *American Physical Therapy Association*, 2007, vol. 87, No. 2, pp. 193-207.

Shaw, D. W. et al., "Influence of normal aging on oral-pharyngeal and upper esophageal sphincter function during swallowing", *American Physiological Society, Am. J. Physiol.*, 1995, vol. 268, pp. G389-G396.

Ship, Jonathan A., DMD et al., "Xerostomia and the Geriatric Patient", *Journal of American Geriatric Society*, 2002, vol. 50, No. 3, pp. 535-543.

Simon, Sidney A. et al., "The neural mechanisms of gestation: a distributed processing code", *Nature Reviews, Neuroscience*, 2006, vol. 7, pp. 890-901.

Sinclair, William J., "Role of the pharyngeal plexus in initiation of swallowing", *American Journal of Physiology*, 1971, vol. 221, No. 5, pp. 1260-1263.

Smith, Stephen M., "Fast Robust Automated Brain Extraction", *Human Brain Mapping*, 2002, vol. 17, pp. 143-155.

Sonies, Barbara C., Ph.D. et al., "Durational Aspects of the Oral-Pharyngeal Phase of Swallow in Normal Adults", *Dysphagia*, 1988, vol. 3, pp. 1-10.

Sörös, Peter et al., "Clustered functional MRI of overt speech production", *NeuroImage*, 2006, vol. 32, pp. 376-387.

Sörös, P. et al., "Functional MRI of Oropharyngeal Air-Pulse Stimulation", *Neuroscience*, 2008, vol. 153, pp. 1300-1308.

Sörös, Peter et al., "Functional MRI of working memory and selective attention in vibrotactile frequency discrimination", *BMC Neuroscience*, 2007, vol. 8, No. 48, pp. 1-10.

Stephen, Jennifer R., MSc et al., "Bolus Location at the Initiation of the Pharyngeal Stage of Swallowing in Healthy Older Adults", *Dysphagia*, 2005, vol. 20, pp. 266-272.

Tanji, J. et al., "Submodality Distribution in Sensorimotor Cortex of the Unanesthetized Monkey", *Journal of Neurophysiology*, 1981, vol. 45, No. 3, pp. 467-481.

Taoka, Miki et al., "Representation of the midline trunk, bilateral arms, and shoulders in the monkey postcentral somatosensory cortex", *Exp Brain Res*, 1998, vol. 123, pp. 315-322.

Theurer, Julie A., MCISc et al., "Oropharyngeal Stimulation with Air-Pulse Trains Increases Swallowing Frequency in Healthy Adults", *Dysphagia*, 2005, vol. 20, pp. 254-260.

Tracy, Julie F., M.A. et al., "Preliminary Observations on the Effects of Age on Oropharyngeal Deglutition", *Dysphagia*, 1989, vol. 4, pp. 90-94.

Van Willigen, J. D. et al., "On the Self-Perception of Jaw Positions in Man", *Archs oral Biol.*, 1983, vol. 28, No. 2, pp. 117-122.

Vandenbergh, Joris et al., "Regional Brain Activation During Proximal Stomach Distention in Humans: A Positron Emission Tomography Study", *American Gastroenterological Association*, 2005, vol. 128, pp. 564-573.

Woolrich, Mark W. et al., "Multilevel linear modeling for FMRI group analysis using Bayesian inference", *NeuroImage*, 2004, vol. 21, pp. 1732-1747.

Yamamoto, Takashi et al., "Taste Responses of Cortical Neurons in Freely Ingesting Rats", *Journal of Neurophysiology*, 1989, vol. 61, No. 6, pp. 1244-1258.

Yoshida, Yoshikazu, MD et al., "Sensory Innervation of the Pharynx and Larynx", *The American Journal of Medicine*, 2000, vol. 108 (4A), pp. 51S-61S.

Yoshida, Kazuya et al., "Somatosensory evoked magnetic fields to air-puff stimulation on the soft palate", *Neuroscience Research*, 2006, vol. 55, pp. 116-122.

Zald, David H. et al., "Cortical Activation Induced by Intraoral Stimulation with Water in Humans", *Chem. Senses*, 2000, vol. 25, pp. 267-275.

Freed M. L. et al., "Electrical stimulation for swallowing disorders caused by strole", *Respir care*, 2001, vol. 46, No. 5, p. 466.

Rosenbek, J. C. et al., "Effects of thermal application on dysphgia after stroke", *J Speech Hear Res*, 1991, vol. 34, No. 6, pp. 1257.

Aviv, Jonathan E. et al., "Surface sensibility of the floor of the mouth and tongue in healthy controls and in radiated patients", *Annual Meeting of the American Academy of Otolaryngology—Head and Neck Surgery*, Kansas City, MO., 1991, pp. 418-423.

Chamberlain, Cheryl K. et al., "Intra-oral tactile sensation and aging in a community-based population", *Aging Clin Exp Res*, 2006, vol. 19, No. 2, pp. 85-90.

Ettlin, D. A. et al., "Cortical Activation Resulting from Painless Vibrotactile Dental Stimulation Measured by Functional Magnetic Resonance Imaging (fMRI)", *J. Dent Res.*. 2004, vol. 83, No. 10. pp. 757-761.

Fujiu, Masako et al., "Glossopharyngeal evoked potentials in normal subjects following n=mechanical stimulation of the anterior faucial pillar", *Electroencephalography and Clinical Neurophysiology*, 1994, vol. 92, pp. 183-195.

Iyengar, Soumya et al., "Cortical and Thalamic Connections of the Representations of the Teeth and Tongue on Somatosensory Cortex of New World Monkeys", *The Journal of Comparative Neurology*, 2007, vol. 501, pp. 95-120.

Jain, Neeraj et al., "Anatomic Correlates of the face and Oral Cavity Representations in the Somatosensory Cortical Area 3b Monkeys", *The Journal of Comparative Neurology*, 2001, vol. 429, pp. 455-468.

Jean, Andre et al., "Inputs to the swallowing medullary from the peripheral afferent fibers and the swallowing cortical area", *Brain Research*, 1979, vol. 178, pp. 567-572.

Jobin, Vincent et al., "Swallowing function and upper airway sensation in obstructive sleep apnea", *J. Appl. Physiol.*, 2007, vol. 102, pp. 1587-1594.

Kim, Il Soo et al., "Influence of Mastication and Salivation on Swallowing in Stroke Patients", *Arch Phys Med Rehabil*, 2005, vol. 86, pp. 1986-1990.

Logemann, Jeri et al., "Effects of a Sour Bolus on Oropharyngeal Swallowing Measures in Patients With Neurogenic Dysphagia", *Journal of Speech and Hearing Research*, 1995, vol. 35, pp. 556-563.

Martin, Ruth E. et al., "Functional Properties of Neurons in the Primate Tongue Primary Motor Cortex During Swallowing", *The American Physiological Society*, 2007, pp. 1516-1530.

Murray, Joseph et al., "The Significance of Accumulated Oropharyngeal Secretions and Swallowing Frequency in Predicting Aspiration", *Dysphagia*, 1996, vol. 11, pp. 99-103.

Nguyen, Anh Tu et al., "Laryngeal and Velopharyngeal Sensory Impairment in Obstructive Sleep Apnea", *Sleep*, 2005, vol. 28, No. 5, pp. 585-593.

Power, M. et al., "Changes in pharyngeal corticobulbar excitability and swallowing behavior after oral stimulation", *Am J. Physiol Garstrointest Liver Physiol*, 2004, vol. 286 pp. G45-G50.

Robbins, JoAnne et al., "Swallowing After Unilateral Stroke of the Cerebral Cortex Preliminary Experience", *Dysphagia*, 1988, vol. 3, pp. 11-17.

Rosenbeck, John C. et al., "Effects of Thermal Application on Dysphagia After Stroke", *Journal of Speech and Hearing Research*, 1991, vol. 34, pp. 1257-1268.

Sessle. Barry J. et al., "Cortical mechanisms controlling mastication and swallowing in the awake monkey", *Brain and oral Functions*, Published by Elsevier Science B.V. 1995, pp. 181-189.

Yamashita, H. et al., "Magnetic sensory cortical responses evoked by tactile stimulations of the human face, oral cavity and flap reconstructions of the tongue", *Eur Arch Otorhinolaryngol*, 1999, vol. 256, pp. S42-S46.

Office Action in Chinese Application No. 200680014928.9, dated Nov. 27, 2009, 6 pgs.

Supplementary EPO Search Report in EP Application No. 06721859.5, dated Nov. 24, 2009, 11 pgs.

* cited by examiner

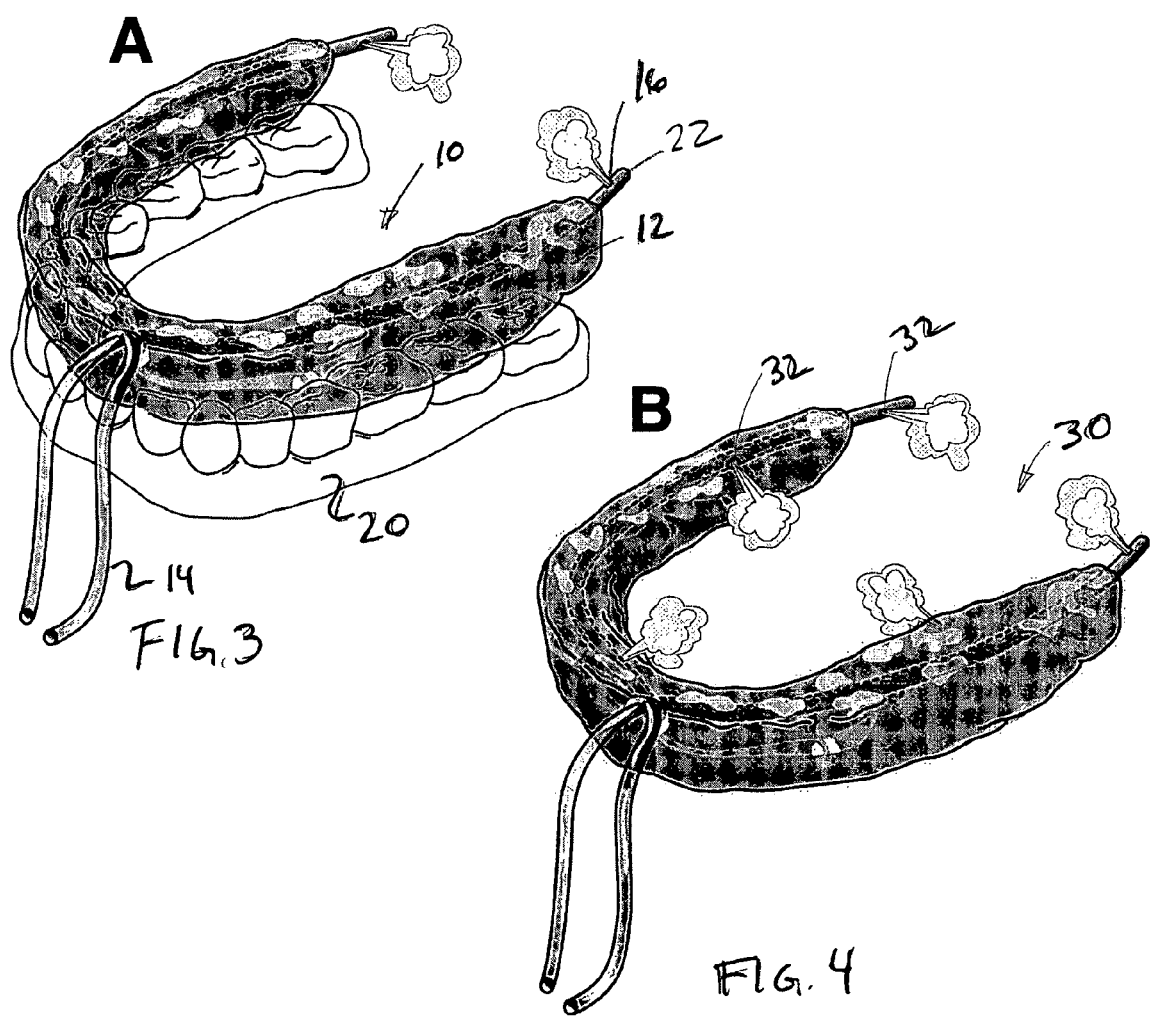

ORAL DEVICE

CROSS REFERENCE TO RELATED PATENT APPLICATION

This patent application relates to U.S. Provisional Patent Application Ser. No. 60/676,942 filed on May 3, 2005 entitled AN ORAL DEVICE which is incorporated herein by reference in its entirety.

FIELD OF THE INVENTION

This invention relates to oral devices and in particular an oral device that may be used as a diagnostic device, or to evoke swallowing, or in other therapeutic oral applications.

BACKGROUND OF THE INVENTION

Swallowing is a complex behaviour in which the output of an integrative brainstem network gives rise to a patterned movement sequence described as the pharyngeal stage of swallowing. While several lines of evidence have demonstrated the importance of oropharyngeal sensory inputs in activating this medullary swallowing network, the range of afferent patterns that are both necessary and sufficient to evoke swallowing has not been fully elucidated. Stimulation of receptive fields innervated by the superior laryngeal nerve (SLN) or the pharyngeal branch of the glossopharyngeal nerve (GPNph) appear to be particularly effective in evoking or modulating the pharyngeal swallow; these "reflexogenic" areas correspond to the laryngeal mucosa, including the epiglottis and arytenoids, the lateral pharyngeal wall, posterior tonsillar pillar and peritonsillar areas.

In humans, the anterior faucial pillar historically has been considered the most reflexogenic site for swallowing. However, the recent finding that the pharyngeal swallow may begin after the bolus head passes the anterior faucial pillars in healthy adults, including geriatric adults, suggests that stimulation of more posterior pharyngeal regions may be required to elicit swallowing. The importance of more posterior oropharyngeal areas in swallowing elicitation is also suggested by anatomic evidence that the human posterior tonsillar pillar, as well as discrete regions of the palate, pharynx and epiglottis are innervated by a dense plexus formed from the GPNph and the vagus nerve. The spatial correspondence between these areas of dual vagal/GPNph innervation and reflexogenic areas for swallowing has lead to the hypothesis that swallowing is elicited most readily by stimulation of areas innervated by both the GPNph and vagus. Dynamic stimuli that excite primary afferents within a number of receptive fields over time appear to elicit swallowing more readily than do static stimuli.

A variety of stimulus modalities have been applied in attempts to evoke swallowing. Repetitive electrical stimulation of the SLN or the GPN, particularly at stimulation frequencies between 30 and 50 Hz, evokes swallowing in a number of animal species. This suggests that the repetitive nature of the stimulus, and the repetition rate, are critical variables in swallowing elicitation. More recently, electrical stimulation of the pharynx has been reported to increase both the excitability and size of the pharyngeal motor cortex representation in humans, and facilitate swallowing in dysphagic patients following stroke. Mechanical and chemical stimuli can evoke swallowing in animal species. In humans, reports on the effects of cold mechanical stimulation of the anterior tonsillar pillar have been variable, some authors reporting decreases in swallowing latency and increases in swallowing frequency, and others failing to find an effect of this type of stimulation on oropharyngeal bolus transit, esophageal coordination, or the temporal pattern of swallowing. Three studies have examined the effects of cold mechanical stimulation applied to the anterior tonsillar pillars in small samples of dysphagic stroke patients. They reported a short-term facilitation of swallowing, measured in terms of reduced delay of the pharyngeal swallow, in some patients, with no related reduction in aspiration. Longitudinal studies, examining the potential long-term effects of oropharyngeal sensitisation on not only swallowing physiology but also on nutritional and respiratory health, have not been reported. Reports on the effects of gustatory stimuli also have been variable. A sour bolus has been reported to facilitate swallowing in stroke patients. Whereas some authors have reported that swallowing latency is significantly reduced by a combination of mechanical, cold, and gustatory (sour) stimulation, others have reported that a cold plus sour bolus reduces the speed of swallowing.

Prior art research shows a novel method for determining laryngopharyngeal sensory thresholds using trains of discrete air pulses delivered endoscopically to the mucosa of the pyriform sinuses and aryepiglottic folds. Sensory thresholds are calculated through psychophysical testing and from elicitation of the laryngeal adduction reflex. The air-pulse train is an interesting stimulus in that it has many of the properties that appear crucial in evoking the pharyngeal swallow. For example, a single air pulse is a dynamic stimulus that could be applied to a number of receptive fields including regions innervated by both the GPNph and SLN. Furthermore, an air-pulse train represents a repetitive stimulus that can be applied at specific frequencies and pressures.

Accordingly, it would be advantageous to provide an oral device that can deliver air-pulse trains to the oral, oropharyngeal or peritonsillar areas. Further it would be advantageous to provide an oral device that facilitates and/or elicits swallowing in adults and children. As well, it would be advantageous to provide an oral device that can provide visual and/or audio feedback responsive to a swallowing attempt. In addition, it would be advantageous to provide an oral device that may be used to improve the motor integrity (e.g., strength, control, tone, accuracy) of the lips, tongue, and/or soft palate, with associated improvements in swallowing, as well as speech production and speech intelligibility.

In addition, recent studies have suggested that the air-pulse train delivered to the oral or oropharyngeal areas results in laryngeal elevation, in some cases associated with a swallow proper. Thus, is would be advantageous to provide an oral device that facilitates or evokes laryngeal movements, such as elevation movements, since laryngeal movement may be a precursor to a swallow proper. It is also clear from previous studies that delivery of an air bolus into the mouth is not the only way in which laryngeal elevation can be achieved. A well-known therapeutic maneuver in swallowing rehabilitation is the 'effortful swallow' in which the patient is simply instructed to swallow effortfully by contracting his/her muscles maximally. This has been shown to result in a more efficient, safer swallow. It has recently been shown that an effortful swallow is associated with increased laryngeal movement. This laryngeal movement can be recorded from a transducer worn around the neck. The amplitude of the output signal from the laryngeal transducer, representing laryngeal movement, is significantly greater in association with an "effortful" swallow, compared to a normal swallow. Other therapeutic maneuvers that also result in increased laryngeal movement include the Mendelsohn Maneuver, supraglottic swallow, super-supraglottic swallow, and the Shaker exercise.

Accordingly it would be advantageous to provide a feedback system that can provide the patient and clinician information about the physiologic correlates of these compensatory swallowing maneuvers, and similar maneuvers that produce laryngeal movement patterns. Certain speech exercises also give rise to laryngeal movement. For example, the pharyngeal squeeze involves producing a vowel sound at a high pitch. This elevates the larynx while at the same time maximally recruiting the pharyngeal muscles. Thus, it is used to strengthen the pharyngeal musculature. Accordingly, it would be advantageous to provide a feedback system that could provide information to the patient and clinician about the laryngeal movement associated with these speech therapy exercises.

SUMMARY OF THE INVENTION

The present invention is an oral device for use with a subject in his/her mouth. The oral device includes at least one conduit for delivering a human non-toxic gas to a predetermined location in the subject's mouth. There is a means for positioning the conduit in the subject's mouth and a means for generating at least one gas pulse through the conduit.

In another aspect of the invention there is provided an oral kit for creating a gas bolus in a subject and monitoring predetermined physical responses. The oral kit includes a means for producing a gas bolus in a subject's mouth; at least one measuring device for measuring the subject's physical responses; and a control system operably connected to the at least one measuring device, the control system having a storing device for storing the measurements from the measuring device.

In a further aspect of the invention there is provided a method of creating a gas bolus in a subject's mouth comprising the step of delivering a gas pulse train to a predetermined area in the subject's mouth.

In a still further aspect of the invention there is provided a method of diagnosing oral sensory abnormality in a subject comprising the step of delivering at least one gas pulse of predetermined amplitude and duration to a predetermined location within the subject's mouth and monitoring the response.

Further features of the invention will be described or will become apparent in the course of the following detailed description.

BRIEF DESCRIPTION OF THE DRAWINGS

The invention will now be described by way of example only, with reference to the accompanying drawings, in which:

FIG. 3 is a perspective view of the oral device of FIG. 1 shown on a dental impression and shown with an air pulse;

FIG. 4 is a perspective view of an alternate embodiment of the oral device of the present invention and showing a plurality of exit holes;

DETAILED DESCRIPTION OF THE INVENTION

Splint Fabrication

Figure 1:
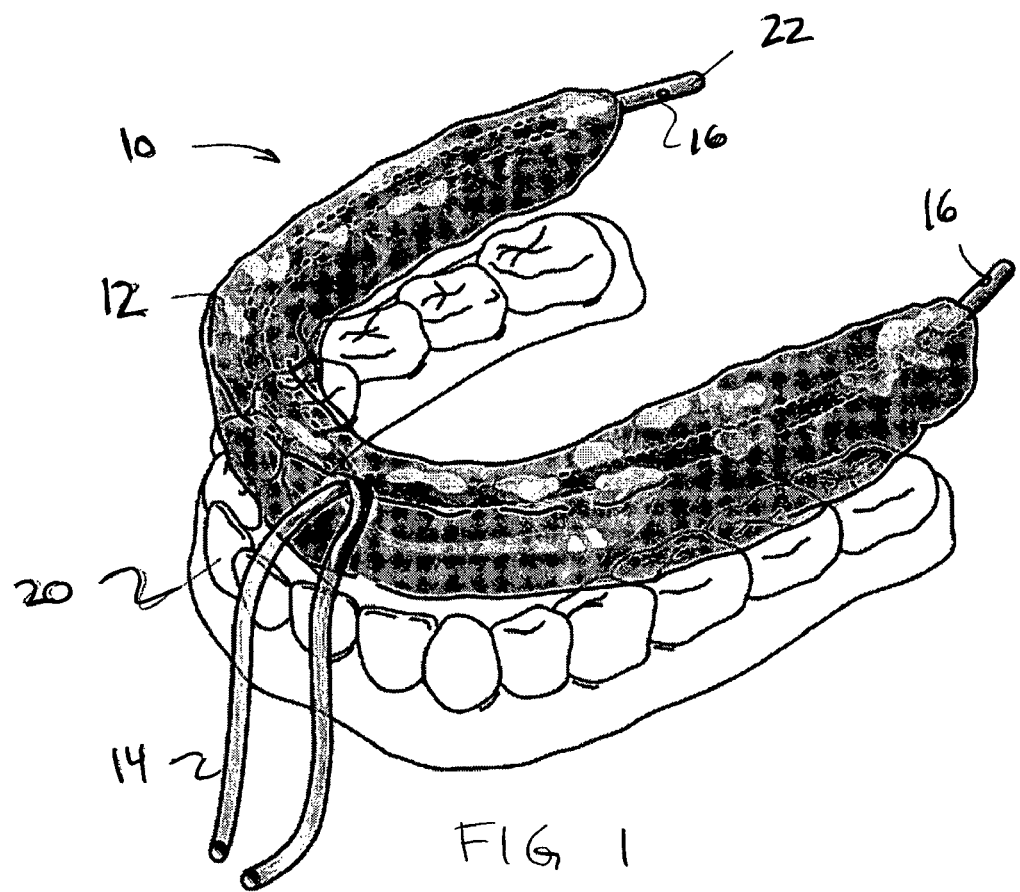
FIG. 1 is a perspective view of an oral device constructed in accordance with the present invention and shown above a dental impression.
Figure 2:
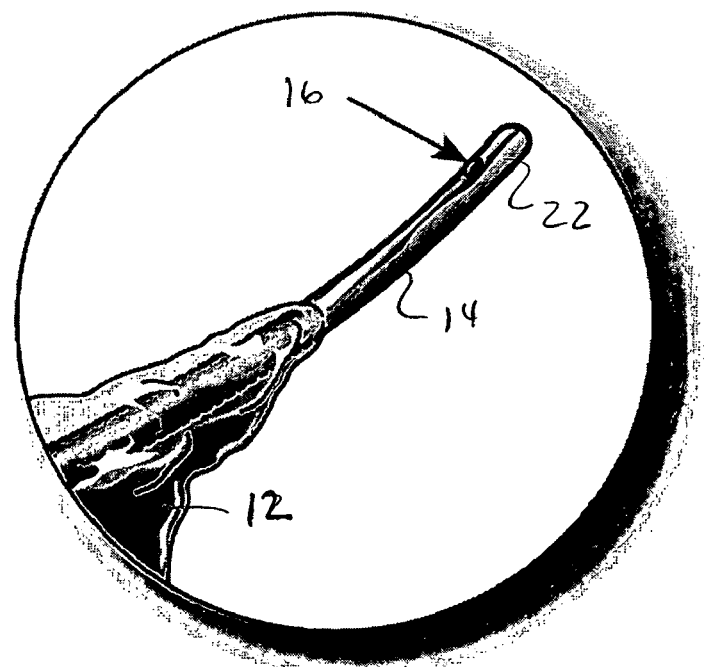
FIG. 2 is an enlarged perspective view of the exit portion of the oral device of FIG. 1.

Referring to FIGS. 1 to 3, the oral device of the present invention is shown generally at 10. The oral device or splint 10 includes a lower dental splint 12 and a means for delivering a gas pulse to a predetermined region in the mouth. The gas pulse delivery means includes at least one conduit or tube 14 having at least one opening 16 at the end thereof positioned such that gas is delivered to a predetermined region in the mouth. Preferably there are two tubes 14 thereby allowing for unilateral stimulation on the left side or the right side of the subject as desired.

Figure 5:
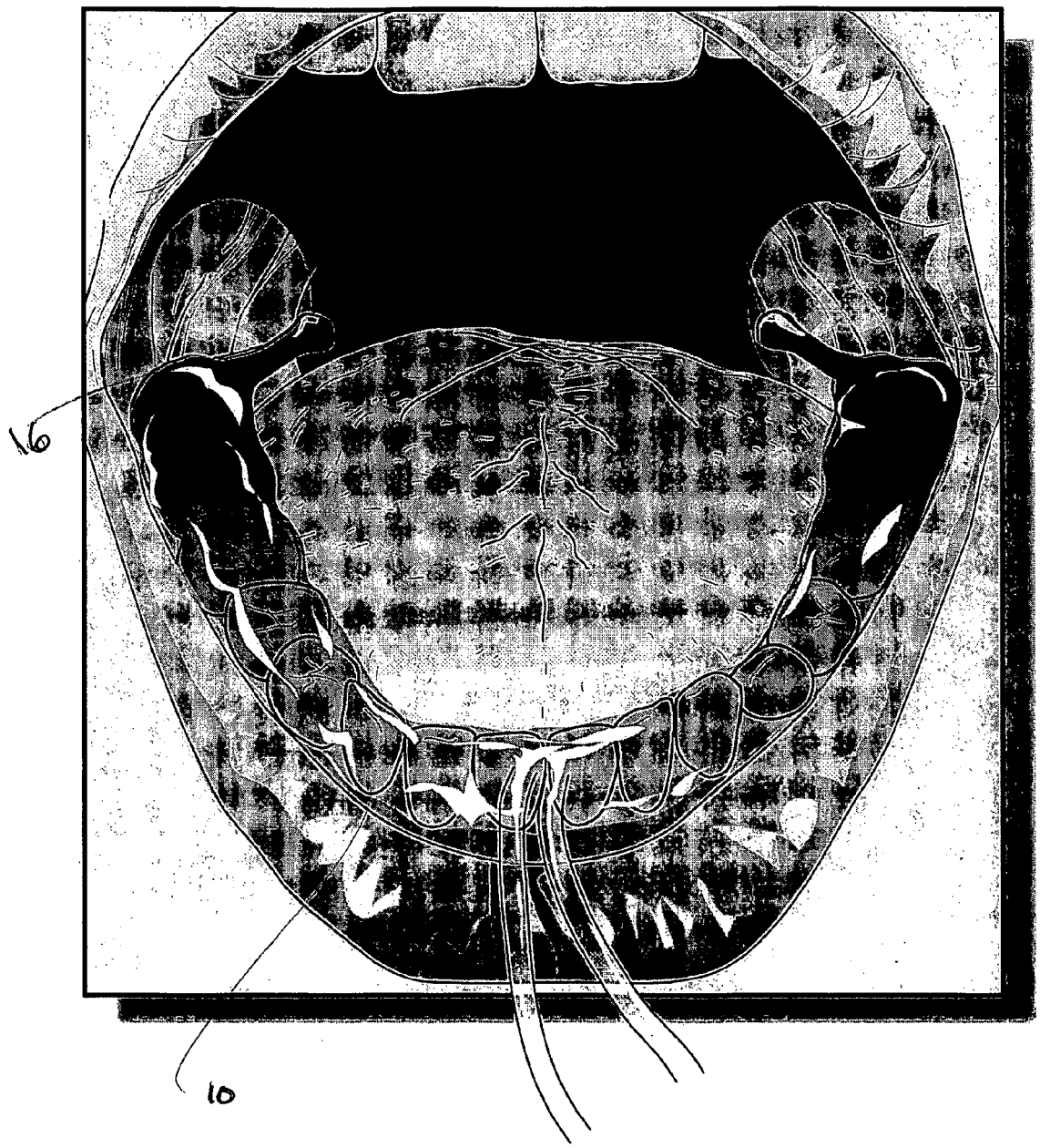
FIG. 5 is a front view of a mouth with the oral device of the present invention positioned therein and showing the air-pulse delivery in the peritonsillar region.
Figure 6:
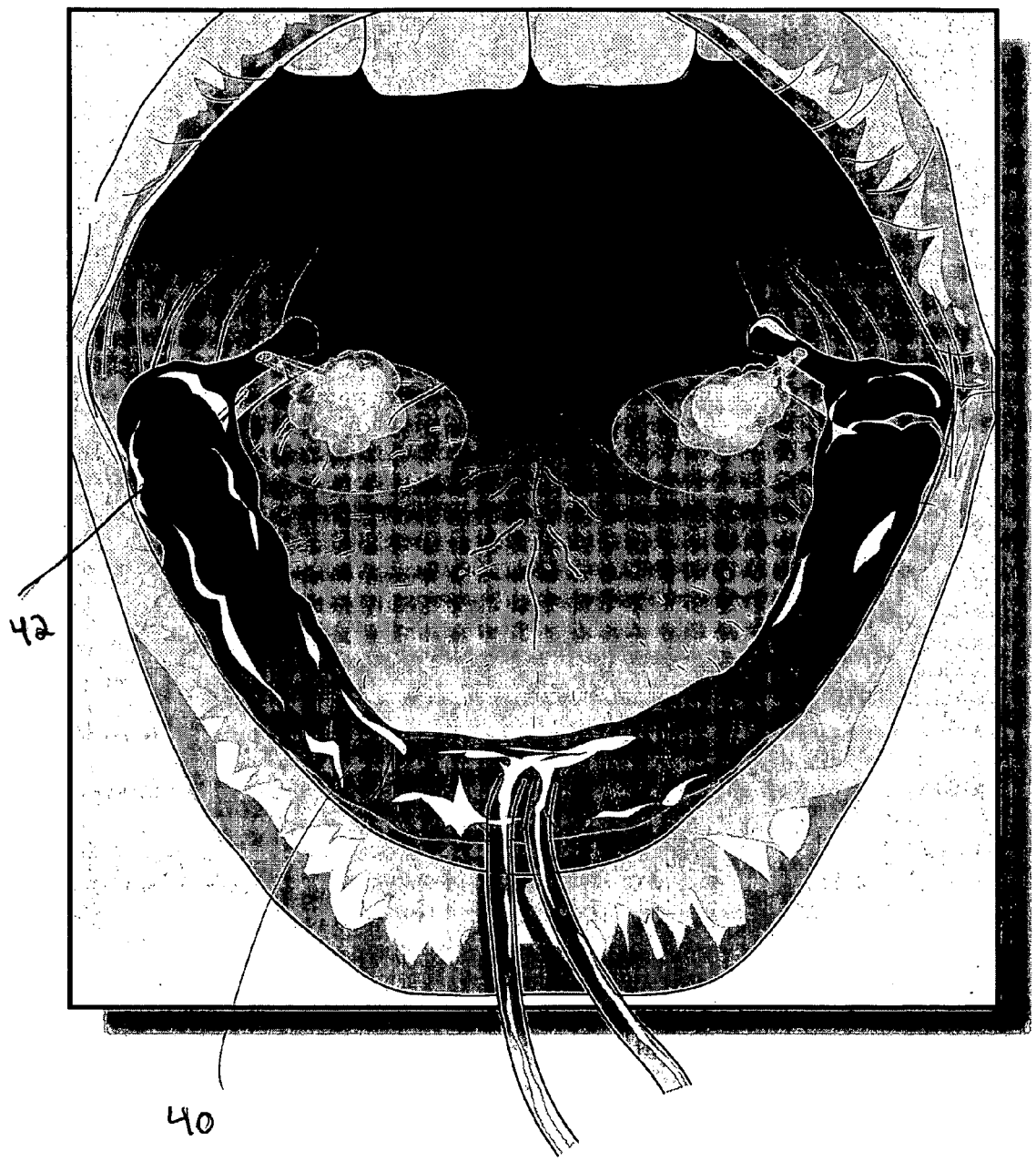
FIG. 6 is a front view of a mouth with the oral device of the present invention positioned therein similar to that shown in FIG. 5 but showing an alternate location of the air-pulse stimulation delivery, namely the tongue.
Figure 7:
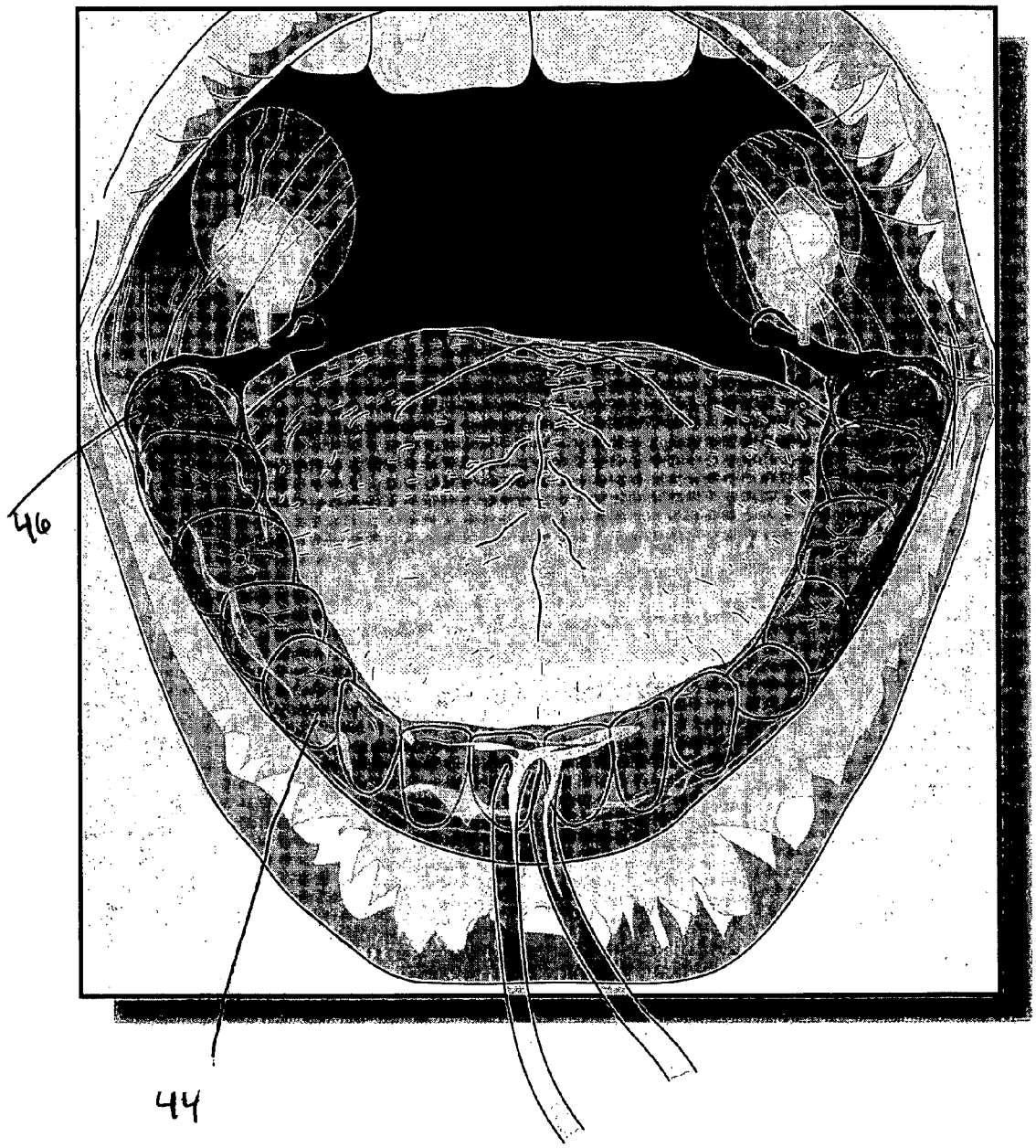
FIG. 7 is a front view of a mouth with the oral device of the present invention positioned therein similar to that shown in FIGS. 5 and 6 but showing an alternate location of the air-pulse stimulation delivery namely, the roof of the mouth or palate.
Figure 10:
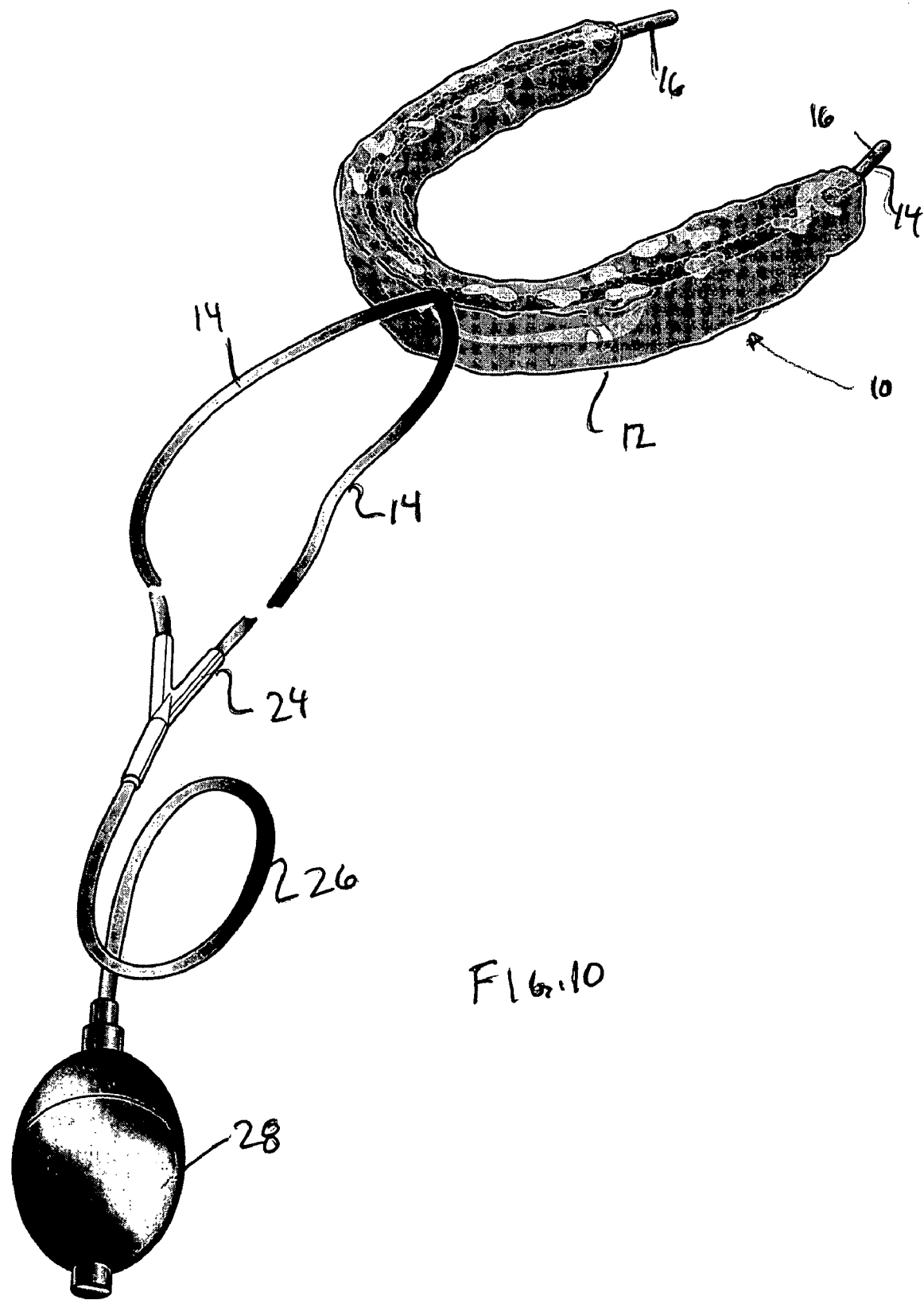
FIG. 10 is a perspective view of the oral device of the present invention showing a hand held air pulse device.

The splint or oral device 10 provides a means of delivering air or gas pulse trains to the peritonsillar region. As well it can be used to deliver air or gas pulse trains to other regions in the mouth. The oral device 10 is preferably made of dental resin that is molded over a dental impression cast 20. Because of a potential effect of jaw opening on the threshold for evoked swallowing, the thickness of the splint 10 is designed to fall within the just-noticeable-difference (JND) for jaw position (i.e., 1-2 mm). Preferably, polyethylene tubing (inner diameter (ID): 1.14 mm, outer diameter (OD): 1.57 mm) attached via silicone to the inferior border of the splint 10 lateral to the alveolar ridge of the mandible and extended approximately 0.1 cm to 1 cm past the posterior edge of the dental splint 10. Optimally, the rigid polyethylene tubing is terminated with human implant grade silicone. Preferably, a 1.5 mm diameter circular opening 16 is formed in the lateral wall of the terminating tubing 14. Opening 16 directs the air or gas pulse trains toward the peritonsillar region of the lateral oropharynx as shown in FIG. 5. Alternatively the air or gas trains can be directed to the tongue as shown in FIG. 6 or the roof of the mouth as shown in FIG. 7. The left and right sides of the splint 10 are fitted with separate tubes 14 to allow for unilateral stimulation conditions. Anteriorly, the tubes 14 from the right and left sides exit the splint 12 within 1 cm of the subject's midline, pass between the subject's lips, are connected to larger diameter polyethylene tubing (preferably 1/16 inch to 1/8 inch inner diameter) and then are connected to a Y-connector 24. The air-pulse trains are generated either (1) manually by the experimenter or user as shown in FIG. 10, or (2) by a electropneumatic control system (see below). Referring to FIG. 10, for the case of manual control, the right and left tubing 14 are connected with a Y-connector 24. Tubing 26 runs from the Y-connector 24 to an air bulb 28 that is manually operated by the experimenter or the subject. The oral device of the present invention may be modified in a number of different ways. For example, as shown in FIG. 4, the oral device or splint 30 may include a plurality of holes 32. The holes 32 are positioned around the splint such that gas or air is pulsed at different locations in the mouth.

FIGS. 5, 6 and 7 show different versions of the oral device at 10, 40 and 44 respectively. As can be seen in the figures the position of the holes 16, 42 and 46 can be arranged such that the air or gas is pulsed onto different locations in the mouth. FIG. 5 shows the pulses directed to the peritonsillar region, FIG. 6 shows the pulses directed to the tongue and FIG. 7 shows the pulses directed to the roof of the mouth. It will be appreciated by those skilled in the art that these regions as shown by way of example only and that the pulses may be directed to a variety of different regions. As discussed above, the utility of the oral device of the present invention may be enhanced by providing feedback in regard to a number of physical responses of the subject. For example by monitoring the laryngeal movement, a swallow may be indicated. In addition, the nature of the swallow may be indicated, such as a weak, or stronger, or satisfactory swallow. An effortful swallow also may be indicated. A central processor connected with a monitor or speaker may be used for visual or auditory feedback to a patient and clinician regarding laryngeal elevation. Within the central processor, the output signals can be compared to preset threshold values such that a correct response signal (visual or auditory) is delivered to the patient if their swallowing behaviour has surpassed some threshold level set by the clinician/caregiver.

Figure 11:
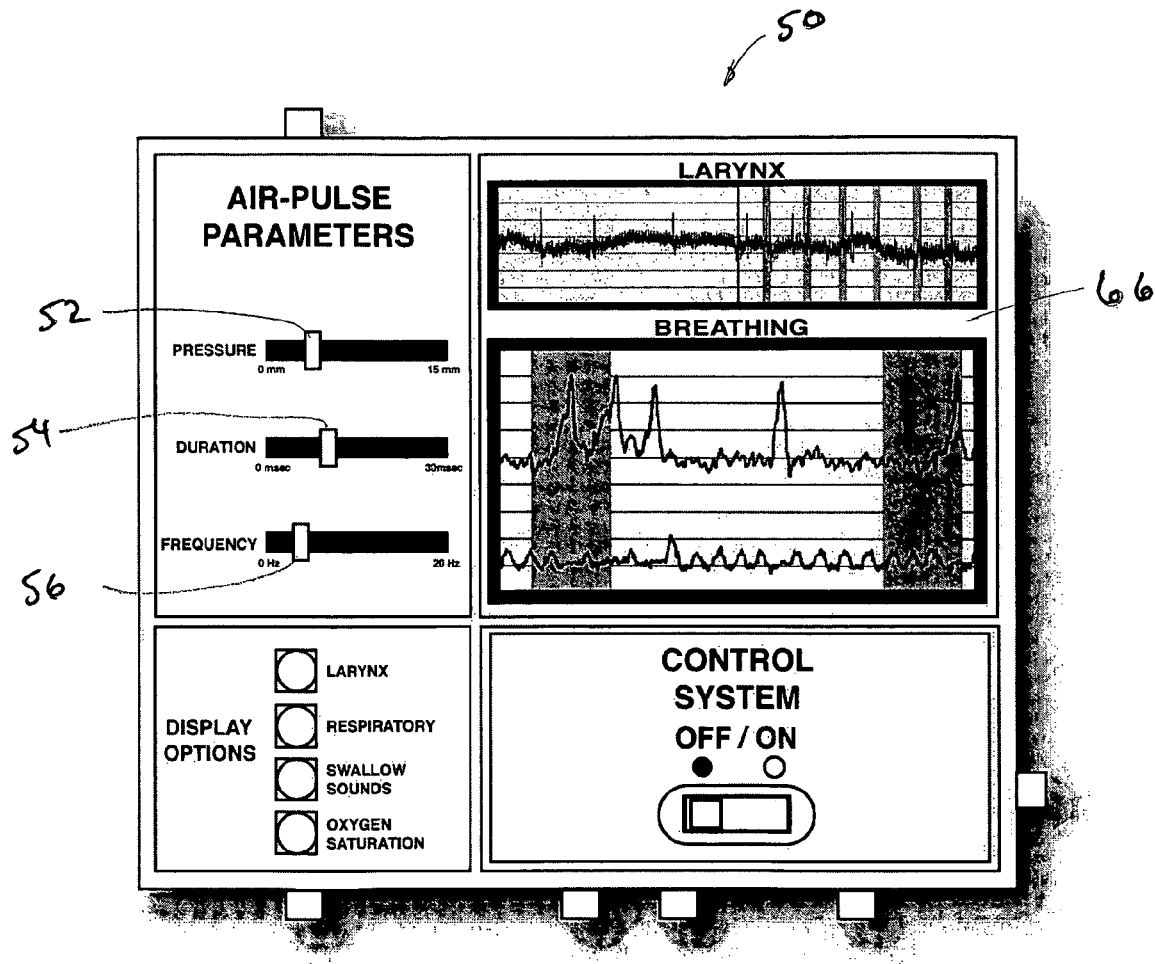
FIG. 11 is a front view of the control system of the oral kit of the present invention.

The oral device 10, 30 of the present invention may be used in conjunction with a control system 50 as shown in FIG. 11. The control system 50 controls the air pulse parameters, specifically the pressure 52, the duration 54 and the frequency 56. In most cases the pulse frequency is in a range from 0.5 to 30 Hz, the pulse train is in a range from 2 and 20 seconds and the pressure is in a range from 3 cm to 15 cm water. In general the gas is air and it is at ambient temperature The control system may also be operably connected to other devices which provide useful feedback when the oral device is used either therapeutically or diagnostically. Preferably the control system also includes feedback from monitoring or measuring devices that measure measurable physical responses. Specifically the control system may be attached to a chest (respiratory) movement sensor 58, a laryngeal movement sensor 60, an accelerometer 62 and/or a pulse oximeter 64 all shown in FIGS. 9 and 10. The chest movement sensor 58 or respiratory movement transducer is for monitoring or measuring the respiratory cycle and periods of swallow-related apnea. The laryngeal movement transducer or sensor 60 is for monitoring or measuring laryngeal elevation/movement associated with swallowing. The accelerometer or throat microphone 62 is for monitoring or measuring the sounds of swallowing. The pulse oximeter 64 is for monitoring the blood oxygen level. Swallowing and tracheal aspiration of ingested material can be associated with decreased blood oxygen saturation. Therefore, it is advantageous for the oral device and kit to include a means of monitoring oxygen saturation of the blood. The outputs from these devices are fed into a central processor or control system 50 and then displayed visually on a monitor 66, or acoustically as auditory feedback via a speaker. Within the central processor, the output signals can be compared to preset threshold values such that a correct response signal (visual or auditory) is delivered to the patient if their swallowing, or oral motor behaviour, has surpassed some threshold level set by the clinician/caregiver. The output signal from the laryngeal movement sensor 60 is displayed as a time course of movement amplitude over time, providing the patient information on laryngeal movement associated with swallowing. This can be used as feedback with respect to swallowing strength, swallowing duration, and therapeutic maneuvers, such as the effortful swallow. It will also indicate the association in time between delivery of air pulses, and associated swallowing responses. This serves not only to enhance learning for the patient, but also to inform the clinician/caregiver regarding the efficacy of air-pulse therapy for an individual patient. The output signal from the respiratory transducer 58 is used in a similar manner, providing both the patient and clinician information on the effects of the air pulses on the respiratory cycles, the association between respiration and swallowing, including coordination of the "swallowing apnea" within the inspiratory and expiratory phases of the respiratory cycle. The signal from the accelerometer 62 provides another means of identifying swallowing—it is a highly "swallow specific" signal, associated with movement of the ingested bolus through the upper sphincter of the esophagus. Thus, when combined with the laryngeal and respiratory signals, it provides a feedback environment for the patient and clinical that is very sensitive and specific to swallowing events. Thus, swallows (in response to air pulse application) can be distinguished from oral movements such as tongue movement for example. The oral device of the present invention could be sold separately or as a kit in conjunction with the control system 50 and one or more of the feedback devices.

The kit could also be used as a patient safety monitoring system. Studies have shown that swallowing accompanied by tracheal aspiration is associated with a greater-than 2% decrease in blood oxygen saturation (see above). Further, some swallowing therapies that involve "bearing down exercises" are associated with cardiac arrythmias in patients with a history of stroke. Therefore, the oral kit of the present invention includes a patient safety-monitoring component that monitors both blood oxygen (with a blood oxygen saturation probe that is worn on the finger) (not shown), and pulse monitor or pulse oximeter 64, and a respiration monitor or chest movement sensor 58. These signals provide the clinician and patient ongoing information about patient safety during therapy/practice sessions.

Figure 8:
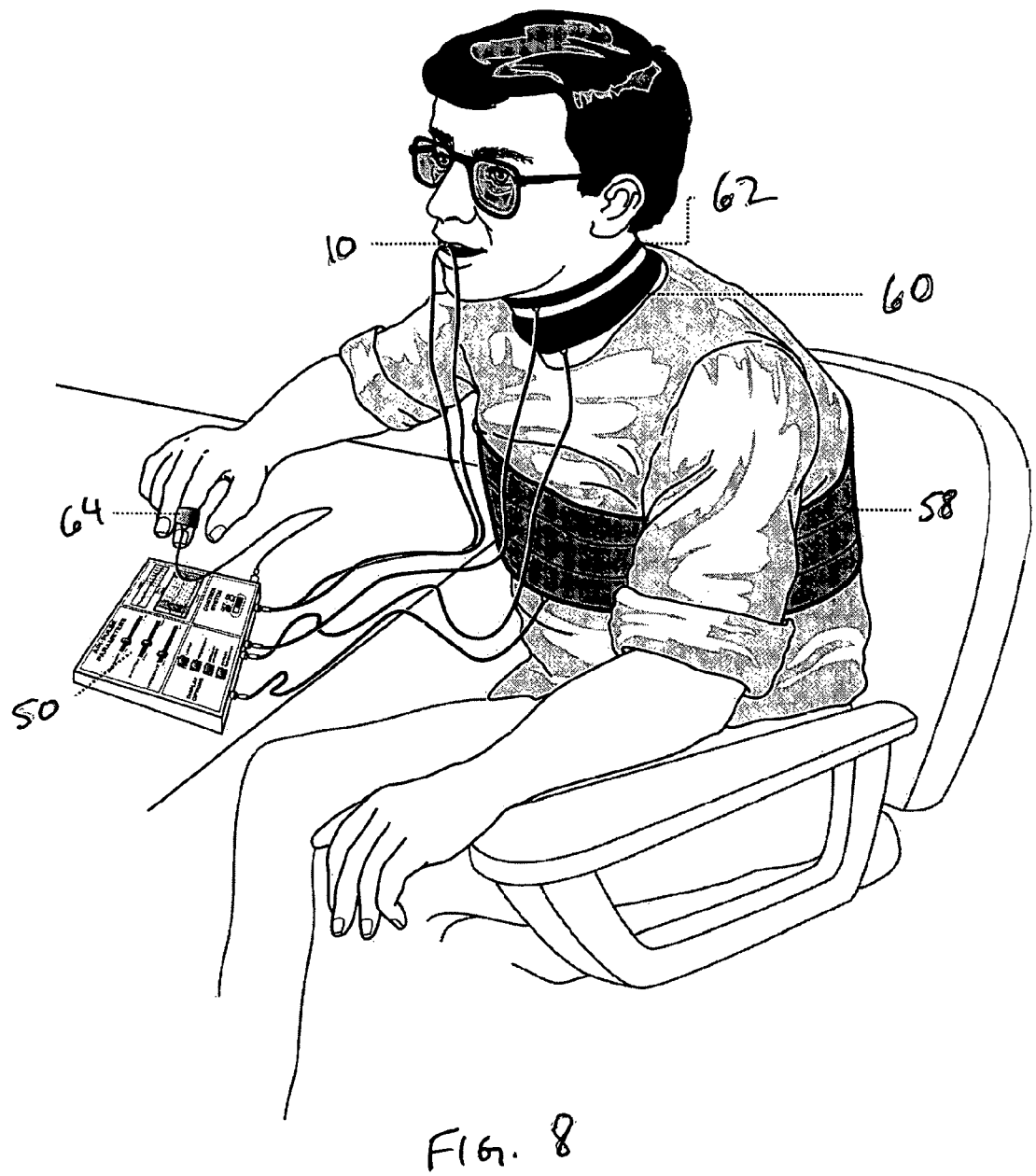
FIG. 8 is a perspective view of a subject in a regular chair using the oral kit of the present invention.
Figure 9:
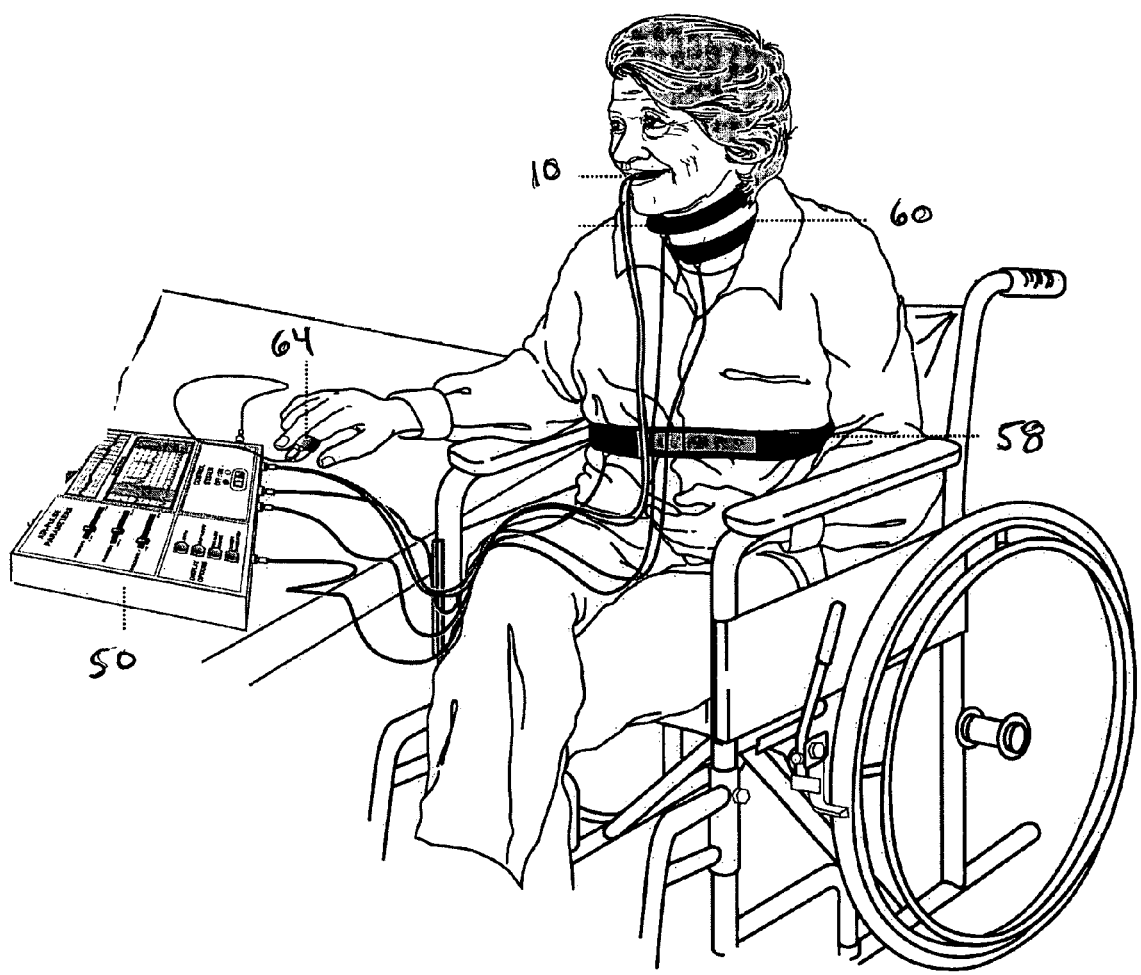
FIG. 9 is a perspective view of the oral kit of present invention which is similar to that shown in FIG. 8 but showing that the device of the present invention may also be used with an older subject in a wheel chair.

It will be appreciated by those skilled in the art that there may be a number of ways that the kit of the present invention may be used. It may be used by a subject who can move around easily and can use a regular chair as shown in FIG. 8. Alternatively it can also be used by an older subject who may have less mobility and therefore uses a wheel chair as shown in FIG. 9.

Control Device for Generating Air-Pulse Trains

The electropneumatic device for controlling the air-pulse trains is controlled from a laptop computer via an I/O card (in/out card). Custom software controls the pulse train air or gas pressure through electropneumatic low air pressure regulators. Custom software also controls air pulse duration, air pulse frequency, and train duration through in-line series solenoids. The pressurized air source is a portable air compressor. The I/O card, air pressure regulator, and solenoids are housed together within a rigid plastic box that also contains all electrical circuitry.

The prescribed air-pulse trains from each of two solenoids flow along rigid polyethylene tubing (preferably inner diameter (ID): 1.14 mm, outer diameter (OD): 1.57 mm). These two lines provided air-pulse sources to the right and left sides of the mouth. Temporal features of the right and left side air-pulse trains are controllable independently to allow for unilateral, or bilateral, stimulation. The tubing 14 enters the subject's mouth within 1 cm of the subject's midline, passing between the subject's lips. The polyethylene tubing 14 is then embedded within an ultra-thin (i.e., 1 mm) lower dental splint 12 made of dental resin, as described above (see FIGS. 1 and 2).

Preferably the pneumatic system is calibrated immediately before each testing/intervention session with the portable manometer. The manometer also allows for on-line verification of air-pulse pressure during experimental/therapeutic sessions.

Subjects

Four right-handed female volunteers with no history of swallowing, orofacial, gastrointestinal, respiratory, or neurological problems were recruited as subjects (age, 30±10.8 yr, mean±SD). A lower dental splint was custom made for each subject.

Experimental Session

The experimental session was conducted in the Orofacial Neuroscience Laboratory at the University of Western Ontario with the subject comfortably seated in a straight-backed chair. At the end of the experimental session, the subject was asked to describe any sensations associated with the stimulation, as well as any responses to the stimulation.

Identification of Swallowing

Figure 12:
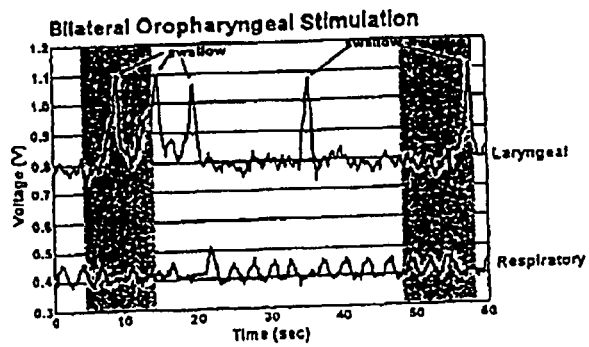
FIG. 12 is a graph showing the laryngeal and respiratory response from bilateral oropharyngeal stimulation.
Figure 13:
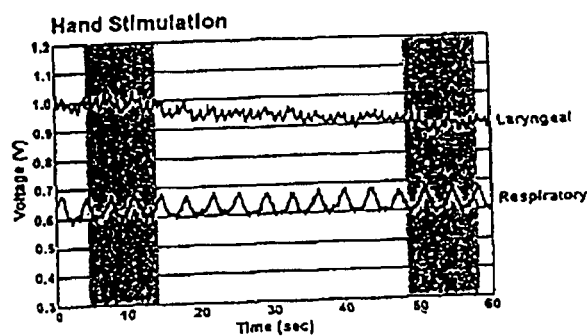
FIG. 13 is a graph showing the laryngeal and respiratory response to hand stimulation.

Laryngeal and respiratory movements were continually recorded, using a digital data acquisition system, throughout the experimental session from the output signals of pressure transducers driven from expanding bellows positioned comfortably around the subject's neck and around the ribcage, respectively. Swallowing was identified on the basis of a distinct pattern of laryngeal movement in association with a transient respiratory apnea (see FIGS. 12 and 13). The number of swallows that occurred within each 5-minute baseline or stimulation period was calculated as the outcome variable for each subject. In addition, the latency of each swallow was calculated relative to the onset of the 10-second air-pulse train immediately preceding the swallow, using the peak of the swallow-related laryngeal movement signal as the indicator of swallowing. Mean swallow latencies were calculated for each subject and for the group.

Task/Stimulation Paradigm

The effects of four air-pulse stimulation conditions on swallowing frequency were examined: right-sided oropharyngeal air-pulse stimulation, left-sided oropharyngeal air-pulse stimulation, bilateral oropharyngeal air-pulse stimulation, and, as a control, unilateral air-pulse stimulation of the dominant (right) hand. Across subjects, the order of the stimulation conditions was randomized; the subjects were blind with regard to the randomization order and were informed only that air-pulse stimulation might be applied either to the mouth or the hand. At the beginning of the experimental session, an adaptation period of 30 minutes provided an opportunity for the subject to adjust to the dental splint. Thereafter, the subject wore the splint throughout the entire experimental session.

Figure 14:
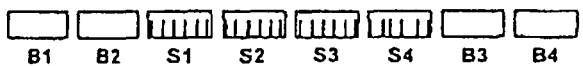
FIG. 14 is a graphical representation of the experimental paradigm showing four air pulse periods between two baseline periods.

During the experimental session, resting laryngeal and respiratory movement data were collected during four 5-minute baseline periods, two immediately preceding, and two immediately following the air-pulse stimulation periods (see FIG. 14). There were four 5-minute air-pulse stimulation periods. Within each of these air-pulse stimulation periods, a total of six 10-second air-pulse trains (repetition frequency=2 Hz, air pressure=6-8 cm $H_2O$) were alternated with stimulation-free periods that varied in duration from 25 to 58 seconds.

Statistical Analysis

Nonparametric statistics were applied based on the small sample size and the nonrandom selection of subjects. A Wilcoxon signed-ranks procedure was used to test for significant differences in the number of swallows produced during (a) the two pre-stimulation baseline periods, (b) the two post-stimulation baseline periods, as well as (c) the pre-stimulation and post-stimulation baseline periods. A Friedman two-way analysis of variance (ANOVA) by ranks, with repeated measures (Factor A=air-pulse stimulation, Factor B=time) was used to examine the effect of air-pulse stimulation on evoked swallowing. The outcomes of multiple pairwise comparisons were judged against a minimum significant difference (MSD) value to determine significant differences between pairs of stimulation conditions. The MSD value was calculated as follows:

$$\text{MSD}=z*\sqrt{([\text{number of subjects}][\text{number of conditions}][\text{number of conditions}+1])/6}, \text{ where } z \text{ is a critical value chosen based on the family-wise error rate } (\alpha_{FW}) \text{ and the number of comparisons being made}$$

Results

Subjective Reports

All subjects reported an irrepressible urge to swallow in response to the oropharyngeal air-pulse stimulation, particularly during the bilateral stimulation condition, followed by an overt swallow as verified by laryngeal and respiratory movements. The stimulus was perceived as contacting the peritonsillar region in all cases. Some subjects described the air-pulse trains as cool in relation to the temperature of the mouth. Some noted that the air-pulse trains increased the total volume of air within the oropharyngeal cavity.

Swallowing Frequency

The mean number of swallows produced during the two pre-stimulation baseline periods, as well as the two post-stimulation periods, were not significantly different (Wilcoxon signed ranks test, p<0.05). Therefore, the data from the two pre-stimulation baseline periods and from the two post-stimulation baseline periods were averaged to obtain a single pre-stimulation baseline period and a single post-stimulation baseline period, respectively, for each subject. Similarly, the numbers of swallows produced during the pre-stimulation and post-stimulation baseline periods were not significantly different and, thus these were also averaged in subsequent analyses. These findings suggest that, by incorporating the 30-minute splint habituation period, a stable swallowing baseline was achieved prior to the oropharyngeal stimulation conditions.

Figure 15:
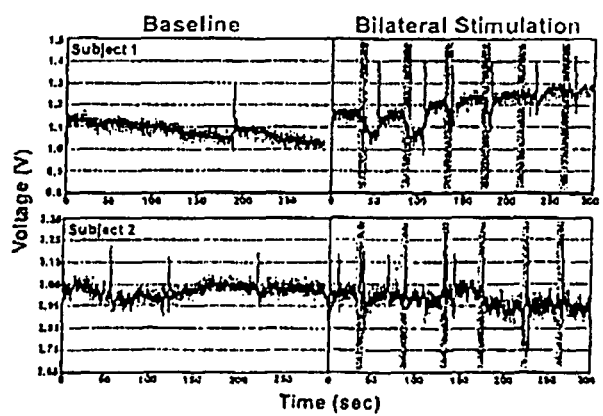
FIG. 15 is a graph showing time course of output of laryngeal bellows positioned around the neck over the thyroid cartilage for Subject 1 and Subject 2.
Figure 16:
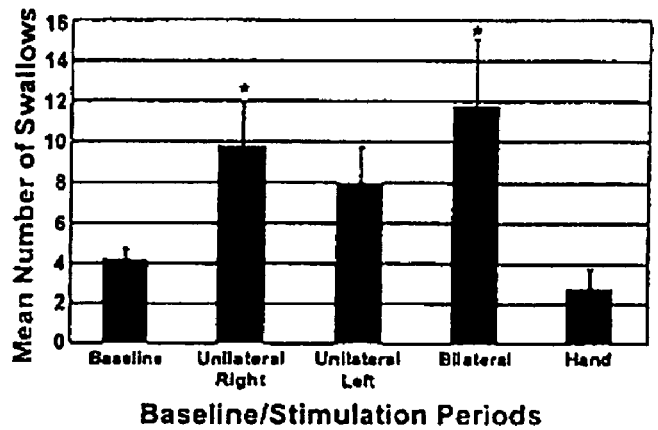
FIG. 16 is a bar graph showing mean number of swallows produced during 5-minute baseline period and 5-minute stimulation conditions.

There was a significant main effect of air-pulse stimulation on swallow frequency (Freidman two-way ANOVA by ranks, p<0.05; FIGS. 15, 16). Multiple pairwise comparisons (MSD=13.1; $\alpha_{FW}$=0.10, 15 pairwise comparisons; one-tailed z=2.475, indicated that swallowing frequency was significantly greater during right oropharyngeal stimulation (9.75±4.43 SD) than during hand stimulation (2.75±1.89 SD), and during bilateral oropharyngeal stimulation (11.75±6.6 SD) compared to hand stimulation. The comparison of bilateral oropharyngeal stimulation and the baseline (4.31±0.88 SD) approached significance. Thus, air-pulse stimulation was associated with a significant increase in swallowing frequency.

Figure 17:
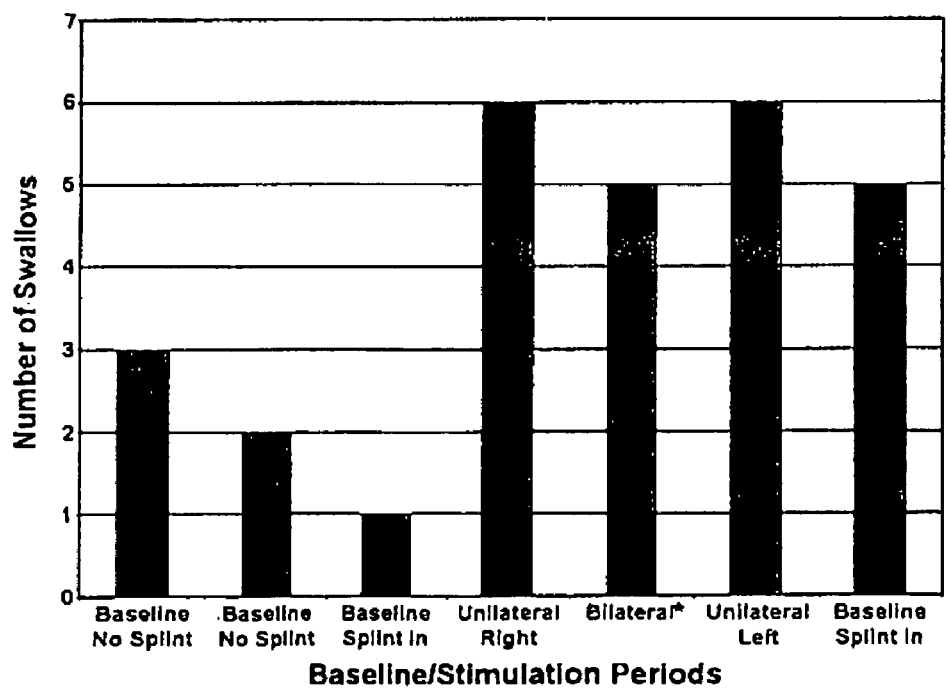
FIG. 17 is bar graph showing mean number of swallows produced during 5-minute baseline period and 5-minute air-pulse stimulation conditions with a subject who had had a stroke.

Results from a similar study with a subject who had suffered a stroke are shown in FIG. 17. Oropharyngeal air-pulse stimulation was associated with a clear increase in swallowing frequency, relative to baseline levels. Thus, a similar effect of the air-pulse application was seen in both the healthy subjects and the subjects with stroke. This suggests that the air-pulse approach may have therapeutic utility in patients with swallowing impairment who have difficulty triggering a swallow. This may include not only persons who have suffered a stroke but also persons who have undergone resection and/or chemoradiation for cancer of the head or neck, persons with various neurological conditions such as cerebral palsy, and Parkinson's disease, or those recovering from traumatic brain injuries.

Swallowing Latencies

The mean swallowing response latencies associated with the bilateral oropharyngeal stimulation tended to be less than the latencies of swallows following unilateral oropharyngeal stimulation (see Table 1). Across subjects and swallowing trials, the swallow latencies ranged from 2.8 to 39.3 seconds. In general, subjects with greater total numbers of swallows per stimulation block demonstrated shorter swallow latencies.

TABLE 1

Mean swallowing response latencies (seconds; mean ± SD) relative to onset of 10-second air-pulse trains for left unilateral, right unilateral and bilateral oropharyngeal stimulation.

| Stimulation | Subject 1 | Subject 2 | Subject 3 | Subject 4 | Group |
|---|---|---|---|---|---|
| Unilateral Left | 12.02 (±15.55) (n = 5) | 7.57 (±2.16) (n = 6) | 22.28 (±6.64) (n = 4) | 15.34 (±3.08) (n = 5) | 13.57 (±9.48) (n = 20) |
| Unilateral Right | 11.42 (±7.52) (n = 6) | 5.3 (±1.79) (n = 6) | 19.05 (±6.59) (n = 4) | 10.48 (±2.48) (n = 5) | 10.9 (±6.74) (n = 21) |
| Bilateral | 6.77 (±2.94) (n = 6) | 4.92 (±1.31) (n = 6) | 23.83 (±10.35) (n = 3) | 9.0 (±5.08) (n = 6) | 9.31 (±7.69) (n = 21) |

(n = number of swallows that occurred during each stimulation condition)

Discussion

Accordingly stimulation of the human oropharynx with air-pulse trains facilitates swallowing, particularly when the stimulation is applied bilaterally. This finding provides support for the widely held view that oropharyngeal sensory stimulation plays an important role in swallowing initiation. It also suggests that oropharyngeal air-pulse stimulation may hold therapeutic potential for some individuals who suffer from dysphagia.

Subjective Reports

All the subjects in the present investigation reported that the air-pulse stimulation evoked a strong, irrepressible urge to swallow. This finding is in contrast to previous investigations that employed other oropharyngeal stimuli and found only a modest swallowing urge accompanied by infrequent swallowing elicitation. The strong urge to swallow documented suggests that the oropharyngeal air-pulse train may be a particularly potent stimulus for evoking swallowing.

The air-pulse trains were perceived by the subjects as evoking a number of oropharyngeal sensations. These included dynamic touch, pressure, and cool temperature. These subjective reports beg the question of what specific attribute(s) of the air-pulse stimulation facilitated swallowing. The peritonsillar area is richly endowed with a variety of sensory receptors including mechanoreceptors and thermoreceptors. The air-pulse train would be expected to excite low-threshold oropharyngeal mechanoreceptors, including those sensitive to moving stimuli. In addition, given that some subjects perceived the air-pulse trains as cool, it is possible that the oropharyngeal thermoreceptors were also excited. Future studies in which properties of the stimulus are independently manipulated are required to clarify the essential properties of the air-pulse trains in eliciting swallowing.

The mechanism through which the air-pulse trains facilitated swallowing should be explored. Local circuits involving GPN and SLN afferent inputs to the medullary swallow center and cranial nerve outputs to the upper aerodigestive tract musculature (3, 31) may mediate the facilitatory effect of the peritonsillar air-pulse stimulation on swallowing. The observed trend that bilateral stimulation was associated with greater swallowing facilitation than unilateral stimulation suggests that an additive mechanism is involved in which sensory inputs from the two sides of the oropharynx summate in initiating swallowing. However, other possible mechanisms are also worth considering. Cortical mechanisms previously implicated in swallowing initiation and control may have contributed to the observed facilitation of swallowing. In addition, an attentional mechanism may have played a role, particularly since the stimulation was suprathreshold. It is noteworthy that the swallowing frequency in the hand condition was slightly less than that during the baseline, suggesting the possibility that attention focused on the sensory stimulation of the hand region had an inhibitory effect on swallowing. Finally, it is possible that the air-pulse trains evoked a secretomotor response resulting in increased salivary flow during the stimulation. While this cannot be ruled out, it would seem unlikely that increased salivary flow would account for the swallows evoked at shortest latency, some of which occurred 2 sec following the stimulation onset. The potential influence of salivation should be examined in future studies.

Limitations

The initial study was preliminary in nature and examined a small sample of subjects. It is likely that intersubject variability within this small sample contributed to the variable results of the planned comparisons, masking some treatment effects. Nevertheless, a significant main effect of air-pulse stimulation found within this limited sample suggests that the facilitatory effect of the oropharyngeal air-pulse trains on swallowing is quite robust.

Other aspects of the methodology also may have influenced the observed effects of the air-pulse stimulation. For example, neither the subjects nor the experimenters were naïve to the focus of the study or the experimental stimulation conditions. Because the stimulation was suprathreshold, the subjects were aware of the stimulation time-course. In addition, the stimulation was controlled by a manually operated pneumatic system that may have introduced variability in the amplitude and duration of the air-pulse trains. Replication studies with blinding of experimenters and subjects, and computer-controlled air-pulse trains are necessary to confirm the present findings.

Clinical Applications

Oropharyngeal sensory stimulation has been advocated as a means of facilitating swallowing in patients suffering from dysphagia. A number of approaches to oropharyngeal stimulation have been reported including manipulating properties of the bolus (e.g., sour bolus, chilled bolus), as well as direct mechanical, thermomechanical, or electrical stimulation applied to the anterior tonsillar pillars or palate. These approaches have achieved substantial clinical acceptance in spite of the fact their efficacy has been difficult to establish. For example, while some authors have reported that cold mechanical stimulation of the anterior tonsillar pillar decreases swallowing latency and increases swallowing frequency, others have failed to find an effect of this type of stimulation on oropharyngeal bolus transit, esophageal coordination, or the temporal pattern of swallowing. Similarly, whereas some authors have reported that swallowing latency is significantly reduced by a combination of mechanical, cold, and gustatory (sour) stimulation, others have reported that a cold plus sour bolus reduces the speed of swallowing. Four studies have examined oropharyngeal sensory manipulations in dysphagic patients following stroke patients. A sour bolus has been reported to facilitate swallowing in stroke. Three studies have examined the effects of cold mechanical stimulation applied to the anterior tonsillar pillars in small samples of dysphagic stroke patients. They reported a short-term facilitation of swallowing, measured in terms of reduced delay of the pharyngeal swallow, in some patients, with no related reduction in aspiration. Longitudinal studies, examining the potential long-term effects of oropharyngeal sensitization, have not been reported.

The present finding that air-pulse trains delivered to the peritonsillar region of the oropharynx are associated with a strong urge to swallow, and a significant increase in swallowing frequency, suggests that oropharyngeal air-pulse stimulation may hold therapeutic potential for some individuals who suffer from dysphagia, including dysphagic individuals who experience delayed triggering of the swallow reflex. Oropharyngeal air-pulse stimulation may be particularly appropriate for individuals who present with an oropharyngeal sensory deficit and/or delayed pharyngeal swallow, for example, secondary to stroke. The inventors' current studies are addressing this exciting clinical question.

It will be appreciated by those skilled in the art that the splint of the present invention could also be used as a diagnostic device. As a diagnostic tool a single or train of air pulses may be used. The location of the air pulse would be determined by the diagnostician. Some locations could be the peri-tonsillar area, the roof of the mouth or palate, or the tongue. The air pulse may be just on one or the other side of the mouth or both sides of the mouth. Air was used herein, however other gases may be used and may be particularly desirable where specific temperatures are required.

It will be appreciated by those skilled in the art that there are few therapies available for individuals with speech and swallowing impairment. The oral device of the present invention delivers calibrated volumes of air to the mouth, that is, an air "bolus". The air bolus increases oral pressure. It has been shown, in healthy controls and in patients with stroke, that air bolus delivery elicits elevation movements of the larynx. Because laryngeal elevation is a central component of swallowing, swallowing can also be elicited as a derivative of the laryngeal elevation. The oral air bolus also appears to increase speech intelligibility, lip strength, and soft palate strength in patients following stroke. The oropharyngeal air-pulse application also increases salivary flow in some patients following stroke. Thus, the oral device of the present invention may also be used to increase saliva production in patients with reduced salivary flow, for example, in patients who have undergone radiation therapy involving the salivary glands in the field of radiation. Accordingly, the oral device of the present invention may also be used for both swallowing therapy and speech therapy.

As used herein, the terms "comprises" and "comprising" are to be construed as being inclusive and open rather than exclusive. Specifically, when used in this specification including the claims, the terms "comprises" and "comprising" and variations thereof mean that the specified features, steps or components are included. The terms are not to be interpreted to exclude the presence of other features, steps or components.

It will be appreciated that the above description is related to the invention by way of example only. Many variations on the invention will be obvious to those skilled in the art and such obvious variations are within the scope of the invention as described herein whether or not expressly described.

What is claimed as the invention is:

1. A method of delivering a gas in a subject's mouth comprising:
    inserting at least one conduit into the subject's mouth, said at least one conduit comprising at least one exit port;
    positioning said at least one conduit in the subject's mouth such that said at least one exit port is directed at a predetermined location in the subject's mouth, and such that said at least one conduit is not disposed between the subject's tongue and a roof of the mouth, wherein said tongue is free to touch said roof of the mouth when said at least one conduit is positioned in the subject's mouth;
    delivering a gas to said predetermined location in the subject's mouth; and
    stimulating said predetermined location in the subject's mouth with said gas and thereby inducing swallowing by the subject with said at least one conduit remaining in the subject's mouth during said swallowing.

2. A method as claimed in claim 1 wherein said delivering said gas comprises delivering said gas at a predetermined frequency between 0.5 and 30 Hz.

3. A method as claimed in claim 2 wherein said delivering said gas comprises delivering a gas pulse train having a duration of between 2 and 20 seconds.

4. A method as claimed in claim 3 further comprising delivering said gas pulse train at a pressure between 3 cm water and 15 cm water.

5. A method as claimed in claim 1 wherein the predetermined location is the peri-tonsillar area.

6. A method as claimed in claim 1 wherein the predetermined location is the tongue.

7. A method as claimed in claim 1 wherein the predetermined location is the roof of the mouth.

8. A method as claimed in claim 1 wherein said at least one conduit is carried by a dental splint.

9. A method as claimed in claim 1 wherein said at least one conduit comprises a plurality of holes formed therein.

10. A method as claimed in claim 1 wherein said gas is air.

11. A method as claimed in claim 1 further comprising closing the subject's jaws with said conduit positioned in the subject's mouth such that a spacing between the subject's jaws is no more than a just noticeable difference for jaw position.

12. A method as claimed in claim 11 wherein said closing the subject's jaw such that said spacing therebetween is no more than said just noticeable difference for jaw position comprises substantially closing said subject's upper and lower teeth such that a space between said upper and lower teeth is less than 2 mm.

13. A method as claimed in claim 12 wherein said space between said upper and lower teeth is between 1 and 2 mm.

14. A method of delivering a gas in a subject's mouth comprising:
   inserting first and second conduits on opposite sides of the mouth, said first and second conduits each comprising at least one exit port;
   positioning said first and second conduits in the subject's mouth such that said exit ports are directed at predetermined locations in the subject's mouth;
   delivering a gas to said predetermined locations in the subject's mouth; and
   stimulating said predetermined locations in the subject's mouth with said gas and thereby inducing swallowing by the subject with said first and second conduits remaining in the subject's mouth during said swallowing.

15. A method as claimed in claim 14 wherein each of said first and second conduits has a hole at the distal end thereof defining said at least one exit port.

16. A method as claimed in claim 14 further comprising separately controlling the delivery of the gas in each of said first and second conduits.

17. A method as claimed in claim 14 wherein said delivering said gas comprises delivering said gas at a predetermined frequency.

18. A method as claimed in claim 14 wherein said delivering said gas comprises delivering said gas at a predetermined pressure.

19. A method as claimed in claim 14 wherein said delivering said gas comprises delivering said gas for a predetermined duration.

20. A method of treating a subject with swallowing impairment comprising:
   inserting at least one conduit into a mouth of a subject suffering from swallowing impairment, said at least one conduit comprising at least one exit port;
   positioning said at least one conduit in the subject's mouth such that said at least one exit port is directed at a predetermined location in the subject's mouth;
   delivering a gas to said predetermined location in the subject's mouth; and
   stimulating said predetermined location in the subject's mouth with said gas and thereby inducing swallowing by the subject with said at least one conduit remaining in the subject's mouth during said swallowing.

21. A method as claimed in claim 20 wherein said subject has had a stroke.

22. A method as claimed in claim 20 wherein said stimulating said predetermined location in the subject's mouth further comprises increasing a frequency of swallowing by said subject's suffering from said swallowing impairment.

23. A method as claimed in claim 20 wherein said stimulating said predetermined location in the subject's mouth further comprises elevating the subject's larynx.

24. A method as claimed in claim 20 wherein said delivering said gas comprises delivering said gas at a predetermined frequency.

25. A method as claimed in claim 24 wherein said predetermined frequency is between 0.5 and 30 Hz.

26. A method as claimed in claim 20 wherein said delivering said gas comprises delivering said gas for a predetermined duration.

27. A method as claimed in claim 26 wherein said delivering said gas at said predetermined duration comprises delivering a gas pulse train having a duration of between 2 and 20 seconds.

28. A method as claimed in claim 20 wherein said delivering said gas comprises delivering said gas at a predetermined pressure.

29. The method of claim 28 wherein said delivering said gas at a predetermined pressure comprises delivering said gas at a pressure between 3 cm water and 15 cm water.

30. The method of claim 20 wherein said at least one conduit comprises first and second conduits positioned on opposite sides of the mouth.

31. The method of claim 20 further comprising separately controlling the delivery of the gas in each of said first and second conduits.

* * * * *

UNITED STATES PATENT AND TRADEMARK OFFICE
CERTIFICATE OF CORRECTION

| | | |
|---|---|---|
| PATENT NO. | : 7,935,065 B2 | Page 1 of 1 |
| APPLICATION NO. | : 11/411241 | |
| DATED | : May 3, 2011 | |
| INVENTOR(S) | : Martin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 925 days.

Signed and Sealed this
Fifth Day of July, 2011

David J. Kappos
*Director of the United States Patent and Trademark Office*